(12) United States Patent
Munro

(10) Patent No.: US 11,944,521 B2
(45) Date of Patent: Apr. 2, 2024

(54) COMPOSITIONS FOR APPLICATION TO WOUNDS

(71) Applicant: FIRST WATER LIMITED, Marlborough (GB)

(72) Inventor: Hugh Semple Munro, Chipping Campden (GB)

(73) Assignee: FIRST WATER LIMITED, Marlborough (GB)

( * ) Notice: Subject to any disclaimer, the term of this patent is extended or adjusted under 35 U.S.C. 154(b) by 703 days.

(21) Appl. No.: 15/775,482

(22) PCT Filed: Nov. 10, 2016

(86) PCT No.: PCT/GB2016/053530
§ 371 (c)(1),
(2) Date: May 11, 2018

(87) PCT Pub. No.: WO2017/081469
PCT Pub. Date: May 18, 2017

(65) Prior Publication Data
US 2019/0000677 A1 Jan. 3, 2019

(30) Foreign Application Priority Data
Nov. 13, 2015 (GB) ..................................... 1520096

(51) Int. Cl.
*A61F 13/02* (2006.01)
*A61F 13/00* (2006.01)
(Continued)

(52) U.S. Cl.
CPC .... *A61F 13/0253* (2013.01); *A61F 13/00063* (2013.01); *A61F 13/0223* (2013.01);
(Continued)

(58) Field of Classification Search
CPC .......... A61F 13/02; A61F 13/023–0266; A61F 13/00063; A61F 13/0223;
(Continued)

(56) References Cited

U.S. PATENT DOCUMENTS 3,416,525 A * 12/1968 Yeremian .......... A61F 13/00029
206/440
4,838,253 A 6/1989 Brassington et al.
(Continued)

FOREIGN PATENT DOCUMENTS

CA 1320085 C 7/1993
CN 1819848 A 8/2006
(Continued)

OTHER PUBLICATIONS

Wacker Chemie AG, Silpuran® "Silicones for wound care".
(Continued)

*Primary Examiner* — Michelle J Lee
(74) *Attorney, Agent, or Firm* — Bookoff McAndrews PLLC

(57) ABSTRACT

Herein is disclosed a composition for application to a wound comprising: a first layer comprising a skin adhesive, wherein the first layer has a wound-facing side and a non-wound-facing side and, in a first area, apertures extend through the first layer from the wound-facing side to the non-wound-facing side; and a second layer disposed on a non-wound-facing side of the first layer, the second layer comprising a polymeric film that is continuous in that it extends over and covers each of the apertures of the first layer, the second layer having a moisture vapour transmission rate (MVTR) of at least 500 g/m²/24 hours, measured in accordance with BS EN 13726-2:2002, wherein the composition further comprises a third layer disposed between the first layer and second layer, the third layer being a supporting layer for the
(Continued)

first layer, the third layer having apertures therethrough, substantially corresponding to the apertures in the first layer. A method of making such a composition is also disclosed.

19 Claims, 9 Drawing Sheets

(51) Int. Cl.
*A61F 13/0203* (2024.01)
*A61F 13/0246* (2024.01)
*A61L 15/26* (2006.01)
*A61L 15/42* (2006.01)
*A61L 15/58* (2006.01)

(52) U.S. Cl.
CPC .............. *A61L 15/26* (2013.01); *A61L 15/425* (2013.01); *A61L 15/58* (2013.01); *A61F 2013/00182* (2013.01); *A61F 2013/00251* (2013.01); *A61F 2013/00263* (2013.01)

(58) Field of Classification Search
CPC .................. A61F 2013/00089–00268; A61F 2013/00855–0088; A61L 15/26; A61L 15/425; A61L 15/58
See application file for complete search history.

(56) References Cited

U.S. PATENT DOCUMENTS

| | | | | |
|---|---|---|---|---|
| 5,010,883 | A | * | 4/1991 | Rawlings ................ A61L 15/58 428/305.5 |
| 5,018,515 | A | * | 5/1991 | Gilman ............... A61F 13/0276 602/45 |
| 5,061,258 | A | * | 10/1991 | Martz ..................... A61L 15/26 604/289 |
| 5,409,472 | A | * | 4/1995 | Rawlings .............. A61F 13/023 602/46 |
| 2004/0127836 | A1 | | 7/2004 | Sigurjonsson et al. |
| 2004/0133143 | A1 | | 7/2004 | Burton et al. |
| 2004/0138604 | A1 | | 7/2004 | Sigurjonsson et al. |
| 2008/0051688 | A1 | * | 2/2008 | Lowe .................... A61F 13/023 602/58 |
| 2010/0179463 | A1 | | 7/2010 | Greener et al. |
| 2010/0292626 | A1 | | 11/2010 | Gundersen et al. |
| 2011/0054374 | A1 | | 3/2011 | Hyde-Edwards et al. |
| 2014/0058309 | A1 | | 2/2014 | Addison et al. |
| 2014/0200529 | A1 | | 7/2014 | Hyde-Edwards |
| 2015/0320605 | A1 | * | 11/2015 | Pigg .................... A61F 13/0206 604/385.05 |

FOREIGN PATENT DOCUMENTS

| | | | |
|---|---|---|---|
| CN | 102076291 A | 5/2011 | |
| CN | 102481208 A | 5/2012 | |
| EP | 0251810 A2 | 1/1988 | |
| EP | 2073771 A1 | 7/2009 | |
| JP | 2011127039 A * | 6/2011 | |
| WO | WO-8801877 A1 * | 3/1988 | |
| WO | WO 02/04200 A1 | 1/2002 | |
| WO | WO 02/13879 A2 | 2/2002 | |
| WO | WO 02/072164 A1 | 9/2002 | |
| WO | WO 03/057103 A1 | 7/2003 | |
| WO | WO 2008/043364 A1 | 4/2008 | |
| WO | WO 2010/056541 A1 | 5/2010 | |
| WO | WO-2011121394 A1 * | 10/2011 | ......... A61F 13/0213 |
| WO | WO 2012/104584 A1 | 8/2012 | |
| WO | WO 2014/003957 A1 | 1/2014 | |
| WO | WO2014097069 A1 | 6/2014 | |
| WO | WO 2015/059501 A1 | 4/2015 | |
| WO | WO 2015/121626 A1 | 8/2015 | |
| WO | WO 2015/140564 A1 | 9/2015 | |
| WO | WO-2016030047 A1 * | 3/2016 | ....... A61F 13/00038 |
| ZA | 1987/04858 | 2/1989 | |

OTHER PUBLICATIONS

Wacker Chemie AG, Safety Data Sheet (1907/2006/EC) Silpuran® 2110 A, Nov. 12, 2015.
Wacker Chemie AG, Safety Data Sheet (1907/2006/EC) Silpuran® 2110 B, Nov. 12, 2015.
International Search Report for PCT/GB2016/053530 dated Feb. 16, 2017 (2 pages).

* cited by examiner

Example 1

Example 2

Example 2 (reference) at start of experiment

Example 2 (reference) after 18 hours, 9ml - failure

Example 2 (reference) – close-up of failed section

Example 1 at start of experiment

Example 1 after 16 hours, 8ml

Example 1 after 24 hours, 12 ml – No failure

Example 2 (reference)

Example 1

COMPOSITIONS FOR APPLICATION TO WOUNDS

This application is a U.S. national stage filing under 35 U.S.C. § 371 of International Patent Application No. PCT/GB2016/053530, filed on Nov. 10, 2016, which claims the benefit of priority to United Kingdom Patent Application No. GB 1520096.7, filed on Nov. 13, 2015.

FIELD OF THE INVENTION

This disclosure relates to compositions and wound dressings.

BACKGROUND OF THE INVENTION

Dressings that cover exuding wounds can, over time, suffer from fluid leakage and/or loss of adherence to the skin of a user. Additionally, some wounds occur on joints of the body, such as a knee or elbow, and a dressing applied to such joints should, ideally, be flexible. However, increasing the adhesion and/or the absorbency of a dressing, e.g. to cope with a highly exuding wound, may decrease the flexibility of the dressing.

In many cases, it is important for a clinician or patient to be able to easily determine whether a wound is healing well or has become infected without removing a dressing. Some optically transparent dressings have been developed in order to allow wounds to be seen without requiring that the dressing be changed too frequently. However, there have appeared to be limits to the fluid-handling capability of such dressings, and they can, over time, suffer from fluid leakage and/or lose adhesion on highly exuding wounds.

Additionally, many wounds produce exudate, which, over time, can significantly reduce the transparency of a dressing. If it is not noticed that the wound is exuding significant amounts of fluid under a dressing, the fluid may leak out of the dressing and/or the dressing may lose adhesion and fail. Leakage of fluid from a dressing typically will break a seal of a dressing with the skin, and form a channel through which bacteria and other microbes can pass into the wound, causing infection. Dressings could be changed more frequently to avoid this problem occurring, but frequent dressing changes can result in damage to the wound and/or the surrounding tissue, particularly for patients with delicate/easily damaged skin.

Thus, dressings that can handle more wound exudate over a given time period and that remain translucent would be advantageous for both patients and clinicians.

Some patients are sight-impaired and, even with a translucent or transparent dressing, may find it difficult to discern whether an underlying wound is exuding a significant amount of fluid and, as such, whether more frequent changes of the dressing may be required.

Some dressings of the prior art include very water-absorbent materials, e.g. some hydrogels, which have a capacity to absorb 500% or more in their own weight in water. Such dressings, while effective in some respects, can lose adhesion when exposed to external water sources, e.g. when a patient bathes in a bath or shower. It is a challenge therefore to produce a dressing having high water-absorbency without the need for highly water-absorbent materials, such as some hydrogels.

It would be desirable to produce a composition or dressing that addresses or mitigates at least one of the problems mentioned above.

SUMMARY OF THE INVENTION

In a first aspect there is provided a composition for application to a wound comprising:
 a first layer comprising a skin adhesive,
  wherein the first layer has a wound-facing side and a non-wound-facing side and, in a first area, apertures extend through the first layer from the wound-facing side to the non-wound-facing side; and
 a second layer disposed on a non-wound-facing side of the first layer, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2:2002,
 wherein the composition further comprises a third layer disposed between the first layer and second layer, the third layer being a supporting layer for the first layer, the third layer having apertures therethrough, substantially corresponding to the apertures in the first layer.

In a second aspect, there is provided a method of forming a composition comprising
 providing a first layer comprising a skin adhesive,
  wherein the first layer has a wound-facing side and a non-wound-facing side and, in a first area, apertures extend through the first layer from the wound-facing side to the non-wound-facing side,
 the first layer being disposed on a third layer, the third layer being a supporting layer for the first layer and having apertures therethrough substantially corresponding to the apertures of the first layer,
 associating a second layer with the first and third layers, such that the third layer is disposed between the first and second layers, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2:2002.

In the first and/or second aspect, optionally, in-use, the wound facing side of the first layer would contact a wound.

In the first and/or second aspect, the skin adhesive may be an adhesive with low water absorption.

In the first and/or second aspect, the first layer may have a second area forming a perimeter around the first area, the perimeter lacking apertures therethrough.

In the first and/or second aspect, the mean area of the apertures on at least one of the wound-facing side and non-wound-facing side of the first layer may be at least 20 mm$^2$.

In the first and/or second aspect, the second layer may be an outermost layer of the composition.

In an embodiment, there is provided a composition for application to a wound comprising:
 a first layer comprising a skin adhesive with low water absorption,
  wherein the first layer has a wound-facing side and a non-wound-facing side and, in a first area, apertures extend through the first layer from the wound-facing side to the non-wound-facing side, the first layer having a second area forming a perimeter around the first area, the perimeter lacking apertures therethrough, and, in-use, the wound facing side of the first layer would contact a wound, wherein the mean area of the apertures on at least one of the wound-facing side and non-wound-facing side of the first layer is at least 20 mm$^2$; and a second layer disposed on a non-wound-facing side of the first layer, the second layer being an outermost layer of the composition, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2:2002, wherein the composition further comprises a third layer disposed between the first layer and second layer, the third layer being a supporting layer for the first layer, the third layer having apertures therethrough, substantially corresponding to the apertures in the first layer.

In an embodiment, there is provided a composition for application to a wound comprising:

a first layer comprising a skin adhesive comprising a substance selected from a silicone, a hydrocolloid, a polyurethane, an acrylic polymer, and a hydrogel, the hydrogel being a hydrogel with low water absorption, wherein the first layer has a wound-facing side and a non-wound-facing side and, in a first area, apertures extend through the first layer from the wound-facing side to the non-wound-facing side, the first layer having a second area forming a perimeter around the first area, the perimeter lacking apertures therethrough, and, in-use, the wound facing side of the first layer would contact a wound, wherein the mean area of the apertures on at least one of the wound-facing side and non-wound-facing side of the first layer is at least 20 mm$^2$; and a second layer disposed on a non-wound-facing side of the first layer, the second layer being an outermost layer of the composition, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2:2002, wherein the composition further comprises a third layer disposed between the first layer and second layer, the third layer being a supporting layer for the first layer, the third layer having apertures therethrough, substantially corresponding to the apertures in the first layer.

In an embodiment, there is provided a method of forming a composition for application to a wound comprising providing a first layer comprising a skin adhesive with low water absorption, wherein the first layer has a wound-facing side and a non-wound-facing side and, in a first area, apertures extend through the first layer from the wound-facing side to the non-wound-facing side, the first layer having a second area forming a perimeter around the first area, the perimeter lacking apertures therethrough, wherein the mean area of the apertures on at least one of the wound-facing side and non-wound-facing side of the first layer is at least 20 mm$^2$, the first layer being disposed on a third layer, the third layer being a supporting layer for the first layer and having apertures therethrough substantially corresponding to the apertures of the first layer, associating a second layer with the first and third layers, such that the third layer is disposed between the first and second layers, the second layer being an outermost layer of the composition, and, in-use, the wound facing side of the first layer would contact a wound, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2:2002.

In an embodiment, there is provided a method of forming a composition for application to a wound comprising providing a first layer comprising a skin adhesive comprising a substance selected from a silicone, a hydrocolloid, a polyurethane, an acrylic polymer and a hydrogel, the hydrogel being a hydrogel with low water absorption, wherein the first layer has a wound-facing side and a non-wound-facing side and, in a first area, apertures extend through the first layer from the wound-facing side to the non-wound-facing side, the first layer having a second area forming a perimeter around the first area, the perimeter lacking apertures therethrough, wherein the mean area of the apertures on at least one of the wound-facing side and non-wound-facing side of the first layer is at least 20 mm$^2$, the first layer being disposed on a third layer, the third layer being a supporting layer for the first layer and having apertures therethrough substantially corresponding to the apertures of the first layer.

associating a second layer with the first and third layers, such that the third layer is disposed between the first and second layers, the second layer being an outermost layer of the composition, and, in-use, the wound facing side of the first layer would contact a wound, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2:2002.

Dressings according to the disclosure herein can have improved fluid handling capabilities over the prior art, yet can be very thin, and relatively simple in their construction. However, their tendency to fail over a given period of time compared to some of the prior art compositions is decreased. If at least some of their components are transparent, e.g. the second layer, they allow an underlying wound to be observed. Furthermore, they have been found to show a doming effect of the second layer overlying the apertures of the third layer when a significant amount of exudate has filled the apertures. This allows a visually impaired person to discern just by touch whether a wound is highly exuding, from which a user can decide when they may wish to change the dressing before leakage or failure of the dressing can occur. They have also been found to be very flexible and suitable for use on joints, while still maintaining adhesion to the skin. At least some of these benefits may be associated with the combination of the relatively large size of the apertures in the first layer, the relatively high MVTR of the second layer, the perimeter of non-apertured area around the aperture area of the first layer, the relatively low water-absorption of the adhesive of the first layer, the presence of the supporting third layer, having apertures corresponding to those of the second layer, and, in some circumstances, other features described herein.

DETAILED DESCRIPTION

Figure 1:
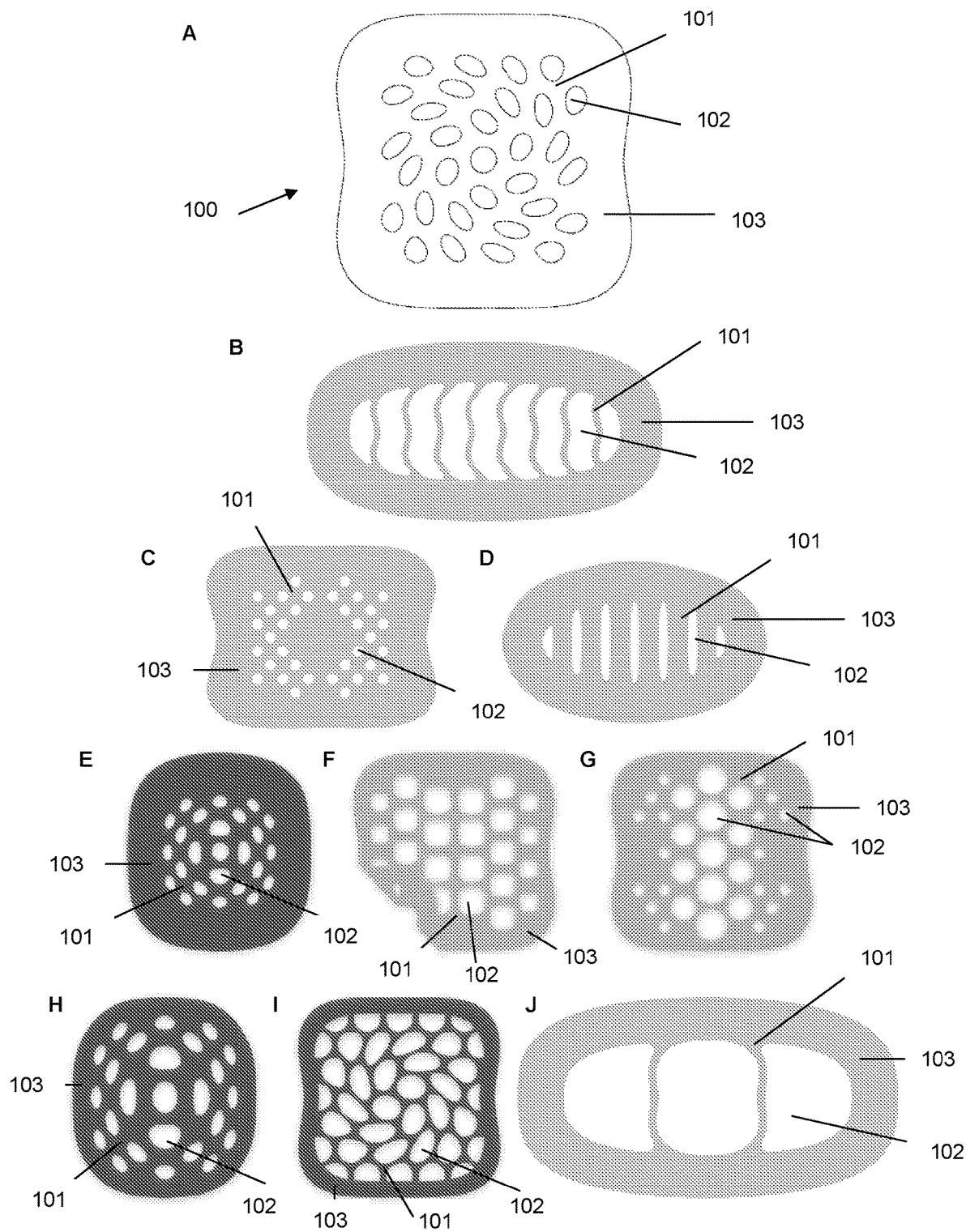
FIG. 1 (A to J) shows schematically, various embodiments of a composition or dressing as described herein from a wound-facing side of the first layer, each dressings having a different array of apertures.

Further aspects, and preferable and optional features of the present disclosure are described below. Any preferable or optional feature may be combined with any other preferable or optional feature and/or with any aspect, unless otherwise stated.

The present invention further provides a method of treating a wound in a human or non-human mammal, particularly a human, comprising contacting the wound for an effective period of time with a composition of the present invention, and wherein the wound-facing side of the layer of first layer is disposed closer to the wound than the non-wound facing side of the first layer. In an embodiment, the wound-facing side of the first layer contacts the wound. In an alternative embodiment, one or more further layers is/are disposed between the wound-facing side of the first layer and the wound.

The present invention further provides the composition as described herein for use in a method of treating a wound in a human or non-human mammal, particularly a human, comprising contacting the wound for an effective period of time with a composition of the present invention, and wherein the wound-facing side of the first layer is disposed closer to the wound than the non-wound facing side of the first layer. In some examples, the wound-facing side of the first layer may be exposed. In other words, the wound-facing side of the first layer may be an outer-most surface of the dressing, at least in use.

A wound to be treated using any of the aspects of the present invention may be of any type, e.g. acute or chronic. The expression "wound" and like expressions, used herein, are intended to cover primarily—but not exclusively—skin lesions in human and other mammalian skin, for example cuts, grazes, abrasions, tears, burns, scalds, ulcers, spots/blisters. The wound can, for example, be dermal, epidermal, or a combination of both.

The wound may for example be a chronic ulcerous skin lesion, for example a malignant or pre-malignant chronic ulcerous skin lesion or a benign chronic ulcerous skin lesion.

The wound may be on a joint of a body, e.g. an elbow or knee.

The wound may be a high exudation wound, a medium exudation wound or a low exudation wound.

Chronic skin lesions arise when a skin wound generally fails to follow an appropriate timely healing process to achieve the normal sustained and stable anatomic and functional integrity of the healed tissue. Generally speaking, a skin lesion which has failed to make at least substantial progress towards healing within a period of at least about three months, or which has become stable in a partially healed state for more than about three months, could be categorised as chronic, although even this general guide is not an absolute marker as the age and fitness of the patient, as well as other factors such as diseases or disorders suffered by the patient (for example, circulatory disorders), can significantly lengthen the normal healing process. A skin lesion which is unhealed after at least about one month, for example after at least about six months, can be categorised as chronic.

The method of the present invention may comprise the contacting of the wound with the composition of the present invention for an effective period of time to promote healing with simultaneous reduction in one or more of pain, exudation, malodour, excoriation, spreading of the wound, tissue necrosis, irritation and hyperkeratosis.

The present invention further provides the use of the composition of the present invention in the preparation of a topical medicament for the treatment of a wound, in a human or non-human mammal, particularly a human.

The present invention further provides a wound dressing comprising, consisting essentially of or consisting of the composition of the present invention.

The mean area of the apertures on at least one of, optionally both of, the wound-facing side and non-wound-facing side of the first layer may be at least 5 $mm^2$. "Mean area of the apertures" is calculated by dividing the total area occupied by the apertures on the wound-facing side or the non-wound-facing side of the first layer by the number of apertures. In an embodiment, the mean area of the apertures on at least one of, optionally both of, the wound-facing side and non-wound-facing side of the first layer is at least 10 $mm^2$. In an embodiment, the mean area of the apertures on at least one of, optionally both of, the wound-facing side and non-wound-facing side of the first layer is at least 20 $mm^2$. In an embodiment, the mean area of the apertures on at least one of, optionally both of, the wound-facing side and non-wound-facing side of the first layer is from about 10 $mm^2$ to about 60 $mm^2$, optionally from about 20 $mm^2$ to about 50 $mm^2$, optionally from about 20 $mm^2$ to about 45 $mm^2$, optionally from about 30 $mm^2$ to about 50 $mm^2$.

In an embodiment, the mean areas of the apertures on at least one of, optionally both of, the wound-facing side and non-wound-facing side of the first layer is at least 30 $mm^2$, optionally at least 40 $mm^2$, optionally at least 50 $mm^2$, optionally at least 100 $mm^2$, optionally at least 200 $mm^2$, optionally at least 300 $mm^2$.

The apertures may be arranged in an array such that there are a plurality of apertures along a direction x across the wound-facing surface of the first layer and a plurality of apertures along a direction y, perpendicular to x, across the wound facing surface of the first layer. The x-direction may be, arbitrarily, taken to be the shortest or longest dimension across the surface of the dressing, i.e. from one edge of the first layer to another edge. A line, when drawn along the x direction may pass over at least 2, apertures, and, optionally, a line, when drawn in the y direction, may pass over at least 2 apertures. A line, when drawn along the x direction may pass over at least 2, optionally at least 3, optionally at least 4, optionally at least 5, optionally at least 6 apertures, and, optionally, a line, when drawn in the y direction, may pass over at least 2, optionally at least 3, optionally at least 4, optionally at least 5, optionally at least 6 apertures.

The apertures may be arranged in an array such that there are a plurality of apertures along a direction x across the wound-facing surface of the first layer and a single of aperture along a direction y, perpendicular to x, across the wound facing surface of the first layer. The x-direction may be, arbitrarily, taken to be the longest dimension across the surface of the dressing, i.e. from one edge of the first layer to another edge. In other words, there may be a single line of apertures in the first layer, and the single line of apertures extends along the longest dimension of the dressing. (In this example, a line, when drawn along the x direction may pass over at least 2 apertures, optionally at least 3, optionally at least 4, optionally at least 5, optionally at least 6 apertures and, optionally, a line, when drawn in the y direction, may pass over only one aperture.) A line, when drawn along the x direction may pass over at least 2, apertures, and, optionally, a line, when drawn in the y direction, may pass over only one aperture. A dressing having such an array has been found to have reasonably high flexibility, and is particularly suitable for placing on a wound over a joint, the line of apertures extending along a direction perpendicular to the axis of the joint (e.g. if the joint is a knee joint, the line of apertures extending along the leg above and below the knee along the length of the leg). In such an arrangement, preferably the apertures are elongate, i.e. having a diameter in a first direction longer than the diameter in a second direction perpendicular to the first direction, with their longest diameter arranged perpendicular to the line of the apertures.

The apertures may have any suitable shape. The apertures may have shapes, when viewed from the wound-facing side and/or non-wound-facing side of the first layer, selected from round, oval, irregular or regular polygonal.

The apertures may be arranged in a repeating pattern. The apertures may have a pattern that has rotational symmetry, e.g. rotational symmetry about a point located on a face of the first layer of the dressing. The rotational symmetry may be n-fold rotational symmetry, where n is 2 or more, e.g. 3, 4, 5 or 6. The apertures may form a pattern of at least one ring around a point located on a face of the first layer of the dressing, and this point may be central or approximately central to the dressing. Optionally, the apertures are round or oval and form a pattern of at least one ring around a point located on a face of the first layer of the dressing, and this point may be central or approximately central to the dressing. Optionally, the apertures are each oval and form a pattern of at least one ring around a point located on a face of the first layer of the dressing, and this point may be central or approximately central to the dressing. "Oval" in the present context include ovaloid, i.e. approximately oval, and perfectly oval. Oval may indicate an aperture with rounded sides, and having an aspect ratio of more than 1, the aspect ratio being the longest distance across an aperture in the plane of the first layer divided by a distance across the aperture in a direction perpendicular to the longest distance. The aspect ratio may be at least 1.2, optionally at least 1.3, optionally at least 1.4. The aspect ratio may be from 1.2 to 2, optionally from 1.3 to 1.9, optionally from 1.4 to 1.8, optionally from 1.5 to 1.7, optionally about 1.6.

In an embodiment, the first layer has a second area forming a perimeter around the first area, the perimeter lacking apertures therethrough. Optionally, for at least one, optionally at least some, optionally all of the apertures, the shortest distance $X_1$ from an aperture in the first layer to an edge of the first layer is at least 3 mm, optionally 5 mm, optionally at least 6 mm, optionally at least 8 mm, optionally at least 10 mm. In other words, the thickness of the perimeter (lacking the apertures) may be at least 3 mm, optionally 5 mm, optionally at least 6 mm, optionally at least 8 mm, optionally at least 10 mm, measured from the edge of the first layer to an aperture closest to the edge, for at least a portion of the perimeter, optionally all around the whole perimeter.

Optionally, for at least one, optionally for at least some, optionally for all the apertures, the shortest distance $X_2$ between a given aperture and an adjacent aperture is at least 2 mm, optionally 2 mm to 20 mm, optionally 2 mm to 15 mm, optionally 2 mm to 10 mm, optionally 3 mm to 7 mm.

The shortest distance $X_1$ from a given aperture in the first layer to an edge of the first layer may be the same as or more than the shortest distance $X_2$ between the given aperture and an adjacent aperture, e.g. the nearest adjacent aperture. Preferably, the shortest distance $X_1$ from a given aperture in the first layer to an edge of the first layer is more than the shortest distance $X_2$ between the given aperture and an adjacent aperture. $X_1/X_2$ may be at least 1.2, optionally at least 1.5, optionally at least 1.7, optionally at least 2. Optionally, for at least some, optionally all of the apertures, the shortest distance $X_1$ from a given aperture in the first layer to an edge of the first layer may be the same as or more than the shortest distance $X_2$ between the given aperture and an adjacent aperture.

The number of apertures in the dressing may be at least 2, optionally at least 3, optionally at least 5, optionally at least 10, optionally at least 15, optionally at least 20.

The cross-section of the apertures may be constant (tubular) through the thickness of the first layer. In other embodiments, the apertures may taper through the thickness of the first layer. This can result in apertures substantially in the form of truncated cones. The apertures will have an opening in the wound-facing side and the non-wound-facing side of the first layer. At least some of the apertures, optionally all of the apertures, may have an opening in the wound-facing side of the layer of first layer that is larger, in area, than the opening in the non-wound-facing side of the first layer. At least some of the apertures, optionally all of the apertures, may have an opening in the wound-facing side of the first layer that is smaller, in area, than the opening in the non-wound-facing side of the first layer.

Preferably, the total area of the apertures on the wound-facing side or non-wound-facing side of the first layer is 70% or less, optionally 60% or less, of the total area of the wound-facing side or non-wound-facing side, respectively, of the first layer. Optionally, the total area of the apertures on the wound-facing side or non-wound-facing side of the first layer is about 10% to about 70%, about 10% to about 60%, optionally about 15% to about 45% of the area of the first layer, optionally about 20% to about 35% of the total area of the wound-facing side or non-wound-facing side, respectively, of the first layer.

The first layer may have from about 1 to about 5 apertures per square 10 cm (10 cm$^2$) of the first layer, for example from about 2 to about 5 apertures per 10 square cm. In certain embodiments the apertures are uniformly distributed over the surface of the first layer, preferably in a regular pattern. Preferably, the apertures are positioned in a central area of the first layer (when viewed from the wound-facing surface of the first layer) with a perimeter of the first layer surrounding the central area, the perimeter having fewer apertures (either in number or in area occupied by the apertures) or the perimeter substantially lacking or lacking apertures.

The first layer comprises a skin adhesive. The skin adhesive may be an adhesive with low water absorption. Low water absorption may be defined such that the skin adhesive has a water absorption such that, when immersed in water at 20° C. for a period of 1 hour, it absorbs 300% or less of its own weight, optionally 250% or less of its own weight, optionally 200% or less of its own weight, optionally 150% or less of its own weight, optionally 120% or less of its own weight, optionally 100% or less of its own weight, optionally 90% or less of its own weight, optionally 80% or less of its own weight, optionally 70% or less of its own weight, optionally 60% or less of its own weight, optionally 50% or less of its own weight, optionally 40% or less of its own weight, optionally 35% or less of its own weight, optionally 30% or less of its own weight. The skin adhesive may be an adhesive with low water absorption, such that the skin adhesive has a water absorption, when immersed in water at 20° C. for a period of 1 hour, it absorbs from 0% to 100% or less of its own weight, optionally 10% to 100% of its own weight, optionally 10% to 70% of its own weight, optionally from 10% to 50% of its own weight, optionally from 10% to 40% of its own weight, optionally from 20% to 40% of its own weight. Skin adhesives with low water absorption may exclude materials such as some hydrogels, which can have a very high water absorption, e.g. over 300% when immersed in water at 20° C. for a period of 1 hour. When immersed in water at 20° C. for a period of 1 hour, the skin adhesive may be present in a layer of, for example, 300 gsm or less (e.g. about 140 g/m² to about 140 g/m²) on a substrate, e.g. a polyurethane film, e.g. a polyurethane film having an (MVTR) of about 2000 g/m²/24 hours, measured in accordance with BS EN 13726-2:2002.

The skin adhesive with low water absorption may be defined as a skin adhesive comprising a substance selected from a silicone, a hydrocolloid, a polyurethane, a rubber adhesive and an acrylic polymer.

The first layer comprises a skin adhesive, and, optionally, the skin adhesive comprises a substance selected from a silicone, a hydrocolloid, a polyurethane, an acrylic polymer, a rubber adhesive and a hydrogel, the hydrogel being a hydrogel with low water absorption. A skin adhesive may be defined as an adhesive that is capable of forming a bond with skin (e.g. human skin).

The skin adhesive may be a pressure-sensitive adhesive. A pressure sensitive adhesive may be defined as an adhesive that forms a bond with a substrate (e.g. human skin) when pressure is applied to the adhesive. Typically, no water, heat or solvent is required to adhere the adhesive to the substrate. The degree of bonding of a pressure sensitive adhesive is typically affected by the pressure used to apply the adhesive to a substrate surface (e.g. human skin).

The skin adhesive, before application of the composition or dressing to the wound, preferably contains a low amount of water, e.g. less than 10 wt % water, optionally less than 5 wt % water, optionally less than 2 wt % water, optionally less than 1 wt % water.

The silicone of the first layer may be a polymer comprising —(SiR$_2$)— repeating units. Each R of the —(SiR$_2$)— may be selected from alkyl or aryl. In an embodiment, the alkyl may be a C1 to C5 alkyl, such as methyl, ethyl, propyl, butyl and pentyl. The alkyl may be straight chain or branched. In an embodiment, the silicone is a polydimethylsiloxane polymer. The silicone may be a cross-linked silicone. The silicone may be a co-polymer, and the co-polymer may comprise a plurality of different types of silicone repeating units, and, in an embodiment, at least some of which are —(SiR$_2$)— repeating units, e.g. wherein each R is methyl, and other silicone units are present that allow cross-linking of the silicone. The silicone may be termed a silicone rubber. The silicone may be formed by addition-curing or condensation curing. The silicone may be formed by addition curing a silicone hydride and a vinyl-functional silicone, e.g. by using a suitable catalyst, such as platinum, forming —(CH$_2$—CH$_2$)— linkages between silicon atoms (the —(CH$_2$—CH$_2$)— being formed from the vinyl group of the vinyl-functional silicone and the hydride (H atom) of the hydride-functional silicone).

The pre-cured silicone preferably has a dynamic viscosity of at least 10,000 mPa s, optionally at least 20,000 mPa s, optionally at least 25,000 mPa s, optionally at least 30,000 mPa s. The viscosity may be measured using the plate/cone method, in accordance with, for example, DIN EN ISO 3219.

The skin adhesive, which may be a pressure sensitive adhesive, may comprise a hydrocolloid. The hydrocolloid may comprise hydrophilic particles and, in some embodiments, a rubber material. The hydrocolloid, or the hydrophilic particles, may be selected from naturally derived substances (such as silica, collagen, pectin, gelatin, starches, guar gum, gum arabic, xanthan gum, locust bean gum, gum karaya, alginic acid and its sodium or calcium salts) and synthetic substances (such as such as sodium carboxymethylcellulose (CMC), crosslinked sodium carboxymethylcellulose, crystalline sodium carboxymethyl cellulose, polyvinyl alcohol, polyvinyl pyrollidone, high molecular weight polyethylene glycols and polypropylene glycols, cross-linked dextran and starch-acrylonitrile graft copolymer, starch sodium polyacrylate, gluten, polymer of methyl vinyl ether and maleic acid and derivatives; polyvinyl pyrrolidone, polyethylene glycols, polypropylene glycols, metal and/or ammonium salts of polyacrylic acid and/or its copolymers, and metal or ammonium salts of polystyrene sulfonic acid) or a variety of alternative commercially available absorbent products. If hydrophilic particles are present in the skin adhesive, they may constitute from about 5%-40%, optionally 20%-40% by weight of the skin adhesive. The rubber material, in which hydrophilic particles may be dispersed, may be selected from natural and synthetic rubbers. The rubber material may comprise a rubber comprising a block co-polymer, e.g. a block co-polymer comprising polydiene, such as isoprene, and a further monomer, e.g. styrene. They may be triblock or di-block co-polymers. The rubber material may comprise a material selected from styrene-isoprene-styrene copolymers, styrene-ethylene/butylene-styrene copolymers, polyisobutylene, and ethylene propylene diene monomer polymer (EPDM polymer).

The pressure-sensitive adhesive may comprise an acrylic polymer. An acrylic polymer may be defined as a polymer that has been formed from the polymerisation of acrylate monomers. The acrylate monomers may be selected from (meth)acrylic acid and esters of (meth)acrylic acid. "(meth)" in (meth)acrylic acid indicates that the monomer may be acrylic acid or methacrylic acid. The pressure-sensitive adhesive may be formed from at least two different acrylate monomers, and optionally the at least two different acrylate monomers may be selected from esters of (meth)acrylic acid and esters of (meth)acrylic acid, and the different acrylate monomers may have different $T_g$ temperatures from one another. The acrylate monomers may be of the formula

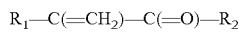

wherein $R_1$ is selected from H and Me, and $R_2$ is selected from H an alkyl group, e.g. a C1-C10 alkyl group. The acrylate monomers may be selected from n-butyl acrylate, 2-ethylhexyl acrylate, acrylic acid, vinyl acetate, and n-butyl methacrylate.

The adhesive of the first layer, which may be a pressure-sensitive adhesive, may comprise a polyurethane. A polyurethane may be defined as the reaction product of a polyisocyanate and a polyalcohol (polyol), the reaction product having urethane linking groups. A polyisocyanate may be defined as a molecule with two or more isocyanate groups. A polyalcohol is may be defined as a molecule with two or more hydroxyl groups. The reaction product is a polymer containing urethane linkages.

The rubber adhesive may be a synthetic or natural rubber adhesive. The rubber adhesive may be a hot melt adhesive. The rubber adhesive may comprise a styrene block copolymer, e.g. a styrene block co-polymer selected from styrene-butadiene-styrene (SBS), styrene-isoprene-styrene (SIS), styrene-ethylene/butylene-styrene (SEBS), styrene-ethylene/propylene(SEP).

The isocyanate may be an aromatic isocyanate or an aliphatic isocyanate. The aromatic isocyanate may be selected from diphenylmethane diisocyanate (MDI) and toluene diisocyanate (TDI). The aliphatic isocyanate may be selected from hexamethylene diisocyanate (HDI) and isophorone diisocyanate (IPDI).

The polyol may, for example, be a polyol formed from polymerising an alkylene oxide, such as propylene oxide (PO) or ethylene oxide (EO), or by polyesterification of a di-acid, such as adipic acid, with glycols, such as ethylene glycol or dipropylene glycol (DPG).

The skin adhesive may comprise a hydrogel, which may be a hydrogel with low water absorption. A hydrogel with low water absorption may be defined such that the hydrogel has a water absorption such that, when immersed in water at 20° C. for a period of 1 hour, it absorbs 300% or less of its own weight, optionally 250% or less of its own weight, optionally 200% or less of its own weight, optionally 150% or less of its own weight, optionally 120% or less of its own weight, optionally 100% or less of its own weight, optionally 90% or less of its own weight, optionally 80% or less of its own weight, optionally 70% or less of its own weight, optionally 60% or less of its own weight, optionally 50% or less of its own weight, optionally 40% or less of its own weight, optionally 35% or less of its own weight, optionally 30% or less of its own weight. The hydrogel may be a hydrogel comprising aqueous plasticiser, for example water in a polyol, for example glycerol polyethylene oxide.

The first layer, e.g. the skin adhesive, may be present on the third layer at a coat weight of 300 gsm or less (grams per square meter), optionally 250 gsm or less, optionally 200 gsm or less, optionally 150 gsm or less. Any weights of the first layer herein (in gsm) is the coat weight of the first layer on the third layer, in areas between the apertures, which may be defined as the coat weight of the first layer on the third layer, before the apertures have been formed in the first and third layers. The first layer may be present in the dressing at a weight of 10 gsm to 300 gsm (grams per square meter), optionally from 50 gsm to 300 gsm, optionally from 100 gsm to 200 gsm, optionally 120 gsm to 170 gsm.

The first layer may comprise a silicone and the first layer may be present on the third layer at a coat weight of 10 gsm to 300 gsm (grams per square meter), optionally from 50 gsm to 300 gsm, optionally from 100 gsm to 200 gsm, optionally 120 gsm to 170 gsm. The measurement of the weight of the first layer is the weight of the continuous part of the first layer, i.e. the part between the apertures, or effectively the weight of the first layer, were it not to have any apertures.

The first layer may comprise a hydrocolloid, and the first layer may be present on the third layer at a coat weight of 10 gsm to 1000 gsm (grams per square meter), optionally from 50 gsm to 1000 gsm, optionally from 80 gsm to 1000 gsm, optionally 80 gsm to 800 gsm, optionally 80 gsm to 500 gsm.

The first layer may comprise a polyurethane, and the first layer may be present on the third layer at a coat weight of 10 gsm to 200 gsm (grams per square meter), optionally from 70 gsm to 130 gsm.

The first layer may comprise a plurality of different types of adhesives, such as any of the adhesives described herein. For example the first layer may comprise first and second adhesives, and, optionally, the first adhesive forms a sublayer (having the apertures therein), and on a wound-facing side of the sublayer (in the areas between the apertures and/or in the perimeter described herein), a discontinuous sublayer of a second adhesive is formed, the second adhesive being different from the first adhesive. The second adhesive may be pattern coated on a wound-facing side of a sublayer of first adhesive (which in turn may be disposed on a wound-facing side of the third layer). In an embodiment, the first adhesive comprises a hydrocolloid or a silicone and the second adhesive comprises an acrylic polymer. The second adhesive may be pattern coated in the form of discrete islands on the first adhesive or in the form of sublayer having apertures therein, such as a net pattern. In an embodiment, the first adhesive comprises a hydrocolloid and the second adhesive comprises a silicone and the second adhesive is pattern coated on the first adhesive.

The first layer may have a peel strength, when part of the composition or dressing, of at least 0.1 N/25 mm, when measured in a 180° peel strength test on steel after 20 minutes adhesion, e.g. a test as described in ASTM D3330, optionally a peel strength of at least 0.3 N/25 mm, optionally a peel strength of at least 0.5 N/25 mm, optionally a peel strength of at least 0.8 N/25 mm, optionally a peel strength of at least 1 N/25 mm, optionally a peel strength of at least 2 N/25 mm, optionally a peel strength of at least 3, N/25 mm, optionally a peel strength of at least 4 N/25 mm, optionally a peel strength of at least 5 N/25 mm.

The first layer may have a peel strength, when part of the composition or dressing, of 10 N/25 mm or less, when measured in a 180° peel strength test on steel after 20 minutes adhesion, e.g. a test as described in ASTM D3330, optionally a peel strength of 8 N/25 mm or less, optionally a peel strength of 6 N/25 mm or less, optionally a peel strength of 5 N/25 mm or less, optionally a peel strength of 4 N/25 mm or less, optionally a peel strength of 3 N/25 mm or less, optionally a peel strength of 2 N/25 mm or less, optionally a peel strength of from 0.01 to 10 N/25 mm, optionally a peel strength of from 0.1 to 5 N/25 mm, optionally a peel strength of from 0.5 to 5 N/25 mm, optionally a peel strength of from 0.5 to 3 N/25 mm, optionally a peel strength of from 0.5 to 2 N/25 mm, optionally a peel strength of about 1 N/25 mm.

The first layer and/or the second layer may be colourless and/or substantially transparent. In an embodiment, the whole composition is colourless and/or substantially transparent. A "colourless" layer in the present context indicates that it substantially lacks a pigment, allowing a colour on a surface immediately beneath the layer in question to be visible through the layer (e.g. when viewed by a human at a distance of 30 cm). A "substantially transparent" layer in the present context indicates that features (e.g. an image) on a surface immediately beneath the layer in question would be visible through the layer (e.g. when viewed by a human at a distance of 30 cm). The features, for the purpose of this test, may be black letters (e.g. A to Z of the roman alphabet) of 12 point height and Times New Roman font on a white background. The "human" in this context may be a human having visual acuity of 6/6 (using meters as a unit of measurement, i.e. a person can see detail from 6 metres away the same as a person with normal eyesight would see from 6 metres).

As described a second layer is disposed on a non-wound-facing side of the first layer. The second layer comprises a polymeric film that is continuous in that it extends over and covers each of the apertures of the first layer. The second layer has a moisture vapour transmission rate (MVTR) of at least 500 g/m$^2$/24 hours, measured in accordance with BS EN 13726-2:2002, optionally at least 600 g/m$^2$/24 hours, optionally at least 800 g/m$^2$/24 hours, optionally at least 1000 g/m$^2$/24 hours, optionally at least 1200 g/m$^2$/24 hours, optionally at least 1500 g/m$^2$/24 hours, optionally at least 1800 g/m$^2$/24 hours, optionally at least 2000 g/m$^2$/24 hours.

The second layer may comprise a polymeric film, which may be or comprise a film comprising a material selected from polyurethane, polyvinylchloride (PVC), poly(ethylene vinyl acetate (EVA)) and poly(ethyl methacrylate (EMA)). The second layer may comprise a polymeric film, which may be or comprise a polyurethane film. Optionally, the polymeric film, which may be or comprise a polyurethane film, is breathable.

Optionally the second layer has a thickness of 0.5 mm to 6 mm. Optionally, the second layer, which may be in the form of a film, has a thickness of 200 µm or less, optionally 150 µm or less, optionally 100 µm or less, optionally 50 µm or less. Optionally, the second layer, which may be in the form of a film has a thickness of 10 µm to 200 µm, optionally 10 µm to 150 µm, optionally 10 µm to 100 µm, optionally 20 µm to 80 µm, optionally 20 µm to 60 µm, optionally 20 µm to 50 µm.

The third layer is disposed between the first layer and second layer. The third layer is a supporting layer for the first layer. The third layer has apertures therethrough, substantially corresponding to the apertures in the first layer. "Substantially corresponding" indicates that at least some of the apertures in the third layer overlie, at least partially, the apertures in the first layer. In an embodiment, the apertures in the third layer are approximately the same size, shape and in the same arrangement as the apertures in the first layer. In an embodiment, the apertures in the third layer overlie the apertures in the first layer and the apertures in the third layer are the same size, shape and in the same arrangement as the apertures in the first layer.

The third layer may be any layer that provides structural support for the first layer comprising an adhesive. The support layer may be present in the form of a sheet of non-adhesive-containing material, which is solid at room temperature (which will be defined as 20° C. herein). The sheet may be in the form of a film, a fabric layer which may comprise natural fibres, synthetic fibres or any combination thereof, and may be woven or non-woven), or a net.

The third layer may comprise a polymeric film, which may be or comprise a film comprising a material selected from polyurethane, polyvinylchloride (PVC), poly(ethylene vinyl acetate (EVA)) and poly(ethyl methacrylate (EMA)). The third layer may comprise a film comprising polyurethane. Optionally the third layer has a thickness of 0.5 mm to 6 mm. Optionally, the third layer, which may be in the form of a film, has a thickness of 200 µm or less, optionally 150 µm or less, optionally 100 µm or less, optionally 50 µm or less. Optionally, the third layer, which may be in the form of a film has a thickness of 10 µm to 200 µm, optionally 10 µm to 150 µm, optionally 10 µm to 100 µm, optionally 20 µm to 80 µm, optionally 20 µm to 60 µm, optionally 20 µm to 50 µm. The third layer may contact the second layer or have a material, e.g. a fourth layer, disposed between the third and second layers. The third layer may be bonded to the second layer by contacting the third and second layer, and effecting bonding between the materials of the third and second layers, e.g. by the application of heat, pressure or suitable means such as ultrasonic energy. The third and second layer may be bonded together by a plastic welding technique selected from flame bonding, using a hot air gun, hot knife welding, hot plate welding, induction/impulse welding, dielectric RF welding, ultrasonic welding and solvent bonding.

In an embodiment, the third layer may be bonded to the second layer by an adhesive disposed between the third and second layer. The adhesive may be a continuous layer of adhesive. In an embodiment the adhesive is in the form of a discontinuous layer of adhesive, e.g. an adhesive in the form of discrete islands on the third layer. The adhesive may form a fourth layer.

In an embodiment, a fourth layer is disposed between the third layer and the second layer, the fourth layer comprising an adhesive. The fourth layer may be continuous and substantially cover the apertures of the first layer or the fourth layer may also have apertures therein substantially corresponding to the apertures in the first and third layers.

In an embodiment, a fourth layer is disposed between the third layer and the second layer, the fourth layer comprising an adhesive, the fourth layer may also having apertures therein substantially corresponding to the apertures in the first and third layers. "Substantially corresponding" indicates that at least some of the apertures in the fourth layer overlie, at least partially, the apertures in the third layer. In an embodiment, the apertures in the fourth layer are approximately the same size, shape and in the same arrangement as the apertures in the third layer and/or first layer. In an embodiment, the apertures in the fourth layer overlie the apertures in the third and first layers and the apertures in the fourth layer are the same size, shape and in the same arrangement as the apertures in the third and first layers.

In an embodiment, the first layer comprises a silicone, the second layer comprises a polyurethane film, the third layer comprises a polyurethane film and the fourth layer comprises an adhesive comprising an acrylic polymer, and optionally the fourth layer has apertures through substantially corresponding to the apertures in the first and third layers.

In an embodiment, the first layer comprises a hydrocolloid, the second layer comprises a polyurethane film, the third layer comprises a polyurethane film and the fourth layer comprises an adhesive comprising an acrylic polymer, and optionally the fourth layer has apertures through substantially corresponding to the apertures in the first and third layers.

In an embodiment, the first layer comprises an acrylic polymer, the second layer comprises a polyurethane film, the third layer comprises a polyurethane film and the fourth layer comprises an adhesive comprising an acrylic polymer, and optionally the fourth layer has apertures through substantially corresponding to the apertures in the first and third layers.

In an embodiment, the first layer comprises an adhesive comprising a polyurethane, the second layer comprises a polyurethane film, the third layer comprises a polyurethane film and the fourth layer comprises an adhesive comprising an acrylic polymer, and optionally the fourth layer has apertures through substantially corresponding to the apertures in the first and third layers.

In an embodiment, the first layer comprises an adhesive comprising a hydrogel, which may be a hydrogel with low water absorption, the second layer comprises a polyurethane film, the third layer comprises a polyurethane film and the fourth layer comprises an adhesive comprising an acrylic polymer, and optionally the fourth layer has apertures through substantially corresponding to the apertures in the first and third layers.

If the third layer comprises a polymeric film, the polymeric film may have a moisture vapour transmission rate (MVTR) of at least 500 g/m$^2$/24 hours, measured in accordance with BS EN 13726-2:2002, optionally at least 600 g/m$^2$/24 hours, optionally at least 800 g/m$^2$/24 hours, optionally at least 1000 g/m$^2$/24 hours, optionally at least 1200 g/m$^2$/24 hours, optionally at least 1500 g/m$^2$/24 hours, optionally at least 1800 g/m$^2$/24 hours, optionally at least 2000 g/m$^2$/24 hours. The MVTR of the third layer is the MVTR of the parts of third layer without apertures, or, in other words, the MVTR of the third layer before apertures have been formed in the third layer.

The fourth layer may comprise an adhesive, which may be different to or the same as the adhesive of the first layer, and may be a pressure sensitive adhesive. In an embodiment, the adhesive of the fourth layer comprises an acrylic polymer, which may be as described above for the first layer. In an embodiment, the adhesive of the fourth layer comprises an acrylic polymer, and the skin adhesive of the first layer comprises a material selected from silicone, a hydrocolloid, an acrylic polymer, a polyurethane and a hydrogel, the hydrogel being a hydrogel with low water absorption. In an embodiment, the adhesive of the fourth layer comprises an acrylic polymer, and the skin adhesive of the first layer comprises a material selected from silicone, a hydrocolloid, and a polyurethane.

In an embodiment, the second layer may be adhered to only portions of the non-wound-facing surface of the third layer. In an embodiment, the fourth layer may be disposed on only part of the non-wound-facing surface of the third layer. In an embodiment, for at least some of the apertures, a portion of the non-wound-facing surface of the third layer surrounding each aperture is not adhered to the second layer, e.g. may be free from adhesive or is not otherwise directly bonded to the second layer by means such as heat. In an embodiment, for at least some of the apertures, a portion of the non-wound-facing surface of the third layer surrounding each aperture is not adhered to the second layer, this portion forming a perimeter around each aperture that is not adhered to the second layer, e.g. may be free from adhesive or is not otherwise directly bonded to the second layer by means such as heat. The width of the perimeter on the third layer around the aperture that is not bonded to the second layer may be at least 0.1 mm, optionally at least 0.2 mm, optionally at least 0.5 mm, optionally from 0.1 mm to 5 mm. Leaving a portion of non-bonded area (i.e. area not bonded to the overlying second layer) around an aperture can increase the doming of the aperture when exposed to exudates from a wound.

The fourth layer, e.g. the adhesive of the fourth layer, which may comprise an acrylic polymer, may be present in the composition or dressing at a weight of 300 gsm or less (grams per square meter), optionally 250 gsm or less, optionally 200 gsm or less, optionally 150 gsm or less. The fourth layer may be present in the composition or dressing at a weight of 10 gsm to 300 gsm or less (grams per square meter), optionally from 10 gsm to 200 gsm, optionally from 20 gsm to 80 gsm, optionally from 20 gsm to 50 gsm, optionally 30 gsm to 60 gsm. The measurement of the weight of the fourth layer is the weight of the continuous part of the fourth layer, i.e. if apertures are present, the part between the apertures, or effectively the weight of the fourth layer, were it not to have any apertures.

The fourth layer may have a peel strength, when coated on the third layer (and before adhesion to the second layer), that is higher than the peel strength of the first layer, when coated on the opposite side of the third layer, the peel strength being measured in a 180° peel strength test on steel after 20 minutes adhesion, e.g. a test as described in ASTM D3330.

The fourth layer may have a peel strength, when coated on the third layer (and before adhesion to the second layer) of at least 2 N/25 mm, when measured in a 180° peel strength test on steel after 20 minutes adhesion, e.g. a test as described in ASTM D3330, optionally a peel strength of at least 5 N/25 mm, optionally a peel strength of at least 7 N/25 mm, optionally a peel strength of at least 8 N/25 mm, optionally a peel strength of from 4 to 10 N/25 mm, optionally a peel strength of from 6 to 10 N/25 mm, optionally a peel strength of about 8 N/25 mm.

The composition or dressing, measured from an outermost face of the first layer to an outermost face of the second layer, may have a thickness of 2 mm or less, optionally 1 mm or less, optionally 500 μm or less, optionally 300 μm or less, optionally 200 μm or less, optionally 100 μm or less. The composition or dressing, measured from an outermost face of the first layer to an outermost face of the second layer, may have a thickness of from 50 μm to 500 μm, optionally from 50 μm to 400 μm, optionally from 50 μm to 300 μm. The thickness of the composition or dressing may be measured using a digital vernier caliper, and preferably, any measurement should be performed using the minimum pressure required for contact with the first and second layers, and preferably the caliper is calibrated prior to measurement. For example, the method of measuring the thickness of a composition or dressing may be by using a commercially available Mitutoyo 0-12.5 mm Digital thickness gauge that is calibrated prior to the measurement. The measurement should be performed using the minimum pressure required for contact.

At least one of the layers, e.g. the first layer, may comprise or having thereon, a bioactive compound. Bioactive compounds that may be mentioned include, for example, pharmaceutically active compounds, antimicrobial agents, antiseptic agents, antibiotics and any combination thereof.

As mentioned, there is provided a method of forming a composition as described herein. Associating in the present context indicates adhering the second layer to the third layer directly (i.e. so that they contact one another), or indirectly (i.e. so that one or more further layers are disposed between the first and second layers, and they adhere together to form the composition or dressing).

The method may comprise a step of forming the apertures in the first layer and third layers.

In an embodiment, before the formation of the apertures in the first layer and third layers, the first layer is disposed on a side of the third layer and the apertures are formed by cutting through the first and third and layers, and, after the apertures have been formed, the third layer is adhered to the second layer.

In an embodiment, before the formation of the apertures in the first layer and third layers, the first layer is disposed on a side of the third layer and a fourth layer comprising an adhesive is disposed on another opposing side of the third layer, and the apertures are formed by cutting through the first, third and fourth layers, and, after the apertures have been formed, the fourth layer is adhered to the second layer. The apertures may be formed by cutting, e.g. die cutting, the apertures. A removable release liner may be present on the adhesive of the first and/or fourth layers during the formation of the apertures in the first, third and fourth layers.

FIGS. 1 to 4 illustrate schematically embodiments of the dressings or compositions as described herein.

FIG. 1 shows several embodiments (A to J) of the dressing or composition (100) described herein, when viewed from an angle perpendicular to the plane of the first layer on a wound-facing side of the first layer. The first layer comprises a first area (101) having apertures (102) extending through the first layer and a second area (103) forming a perimeter around the first area, the perimeter lacking apertures therethrough. The apertures (102) are arranged in an array as shown. In each of the embodiments, a second layer (not shown in FIG. 1) is disposed on a non-wound-facing side of the first layer and extends over all of the layer, covering all of the apertures. The second layer comprises a polymeric film having a moisture vapour transmission rate (MVTR) of at least 500 g/m$^2$/24 hours. A third layer (not shown in FIG. 1) may be disposed between the first layer and second layer, the third layer being a supporting layer for the first layer and having apertures therethrough, substantially corresponding to the apertures in the first layer. Thus, for each embodiment, the shape/structure/form of the third layer may substantially correspond to that shown in FIG. 1.

In some embodiments of FIG. 1, the apertures are arranged to form a linear array such as that shown in FIGS. 1B, D and J. In these linear arrays, a single line of apertures is provided in the first layer. In other arrays, a plurality of aperture are provided in each of the x and y dimensions of the plane of the first layer (x direction being left to right across the figure, y direction being up and down when looking at the figure). In some embodiments, the apertures forming the first area surround a third area which lacks apertures therethrough, for example, as shown in FIG. 1 C.

In FIG. 1F, an embodiment is shown with one corner (bottom left when the figure is viewed) folded over the main portion of the embodiment.

Figure 1K:
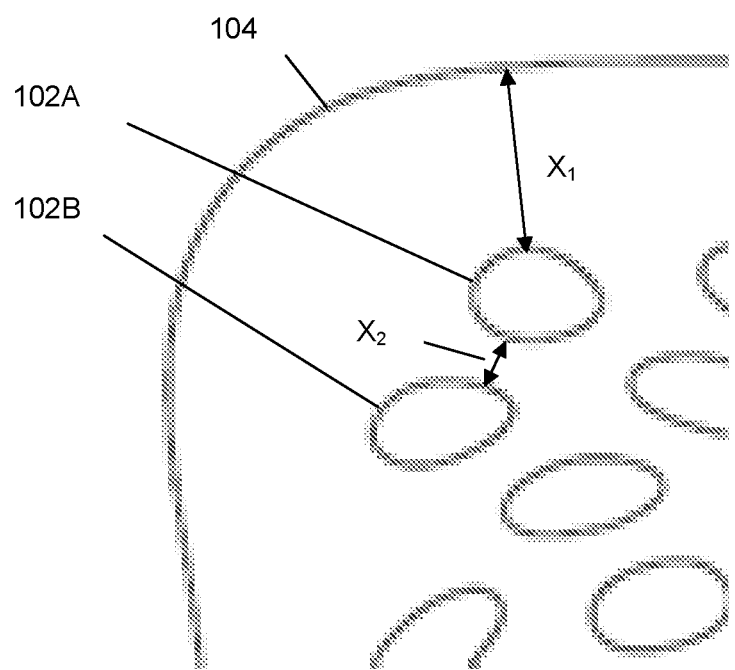
FIG. 1K is an enlarged view of part of FIG. 1A.

FIG. 1K is an enlarged view of part of FIG. 1A (namely the upper left corner of FIG. 1A). Here it is shown, for a given aperture (102A in this case, although any aperture could be chosen), the shortest distance ($X_1$) between the aperture (102A) and the edge (104) of the first layer. Also shown is the distance ($X_2$) from the given aperture (102A) to the nearest adjacent aperture (102B). It can be seen that $X_2$ is more than $X_1$.

Figure 2:
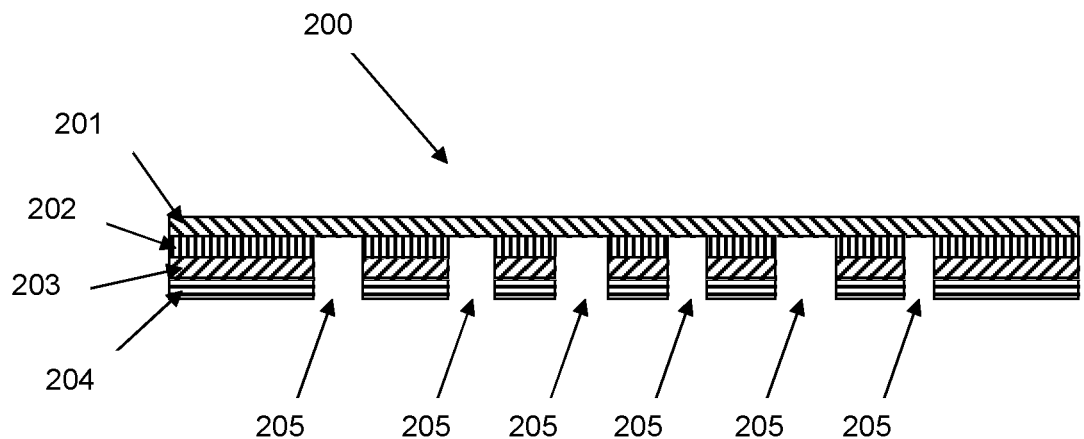
FIG. 2 shows schematically a cross-sectional view of an embodiment of the composition or wound dressing as described herein having a layer of silicone pressure-sensitive adhesive.

FIG. 2 shows schematically a cross-sectional view of an embodiment of the composition or wound dressing (200) described herein. In this embodiment, a layer (denoted a first layer herein) of skin adhesive comprising a silicone (204) is shown, the skin adhesive having apertures (205) extending therethrough. A supporting film (203) overlies and is in contact with the first layer; this film (203) corresponds to a third layer as described herein. An adhesive layer (202) overlies the supporting film; this adhesive layer (302) corresponds to a fourth layer as described herein. The supporting film (203) and adhesive layer (202) each have apertures therein overlying the apertures (205) in the first layer (204). The apertures in the supporting film (203) and adhesive layer (202) are of approximately the same size, shape and location as the apertures (205) in the first layer. A polymeric backing film (201) is adhered to the adhesive layer (202), the backing layer being continuous, in that it extends over and covers each of the apertures in the first layer; the polymeric backing film corresponds to the second layer described herein.

Figure 3:
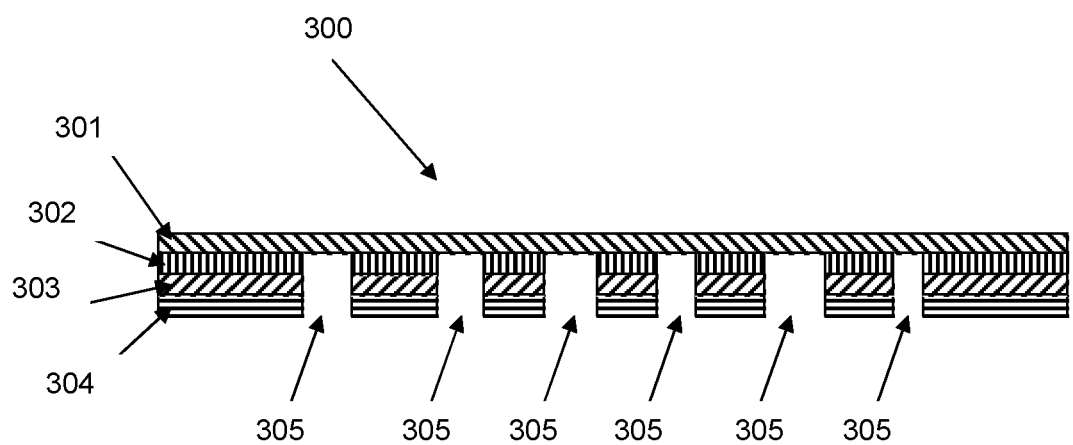
FIG. 3 shows schematically a cross-sectional view of an embodiment of the composition or wound dressing as described herein having a layer of hydrocolloid pressure-sensitive adhesive described herein.

FIG. 3 shows schematically a cross-sectional view of an embodiment of the composition or wound dressing (300) described herein. In this embodiment, a layer (denoted a first layer herein) of skin adhesive comprising a hydrocolloid (304) is shown, the skin adhesive having apertures (305) extending therethrough. A supporting film (303) overlies and is in contact with the first layer; this film (303) corresponds to a third layer as described herein. An adhesive layer (302) overlies the supporting film; this adhesive layer (302) corresponds to a fourth layer as described herein. The supporting film (303) and adhesive layer (302) each have apertures therein overlying the apertures (305) in the first layer (304). The apertures in the supporting film (303) and adhesive layer (302) are of approximately the same size, shape and location as the apertures (305) in the first layer. A polymeric backing film (301) is adhered to the adhesive layer (302), the backing layer being continuous, in that it extends over and covers each of the apertures in the first layer; the polymeric backing film corresponds to the second layer described herein.

Figure 4:
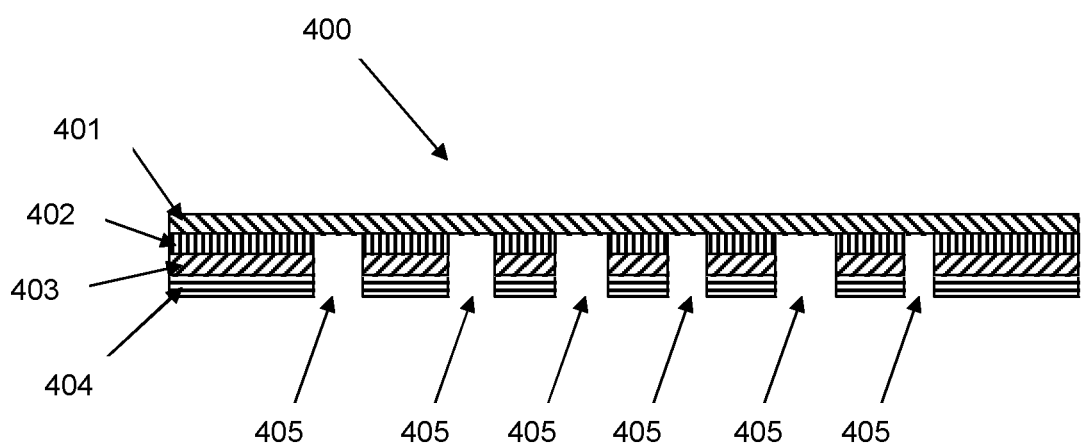
FIG. 4 shows schematically a cross-sectional view of an embodiment of the composition or wound dressing as described herein having a layer of acrylic polymer pressure-sensitive adhesive described herein.

FIG. 4 shows schematically a cross-sectional view of an embodiment of the composition or wound dressing (400) described herein. In this embodiment, a layer (denoted a first layer herein) of skin adhesive comprising an acrylic polymer (404) is shown, the skin adhesive having apertures (405) extending therethrough. A supporting film (403) overlies and is in contact with the first layer; this film (403) corresponds to a third layer as described herein. An adhesive layer (402) overlies the supporting film; this adhesive layer (402) corresponds to a fourth layer as described herein. The supporting film (403) and adhesive layer (402) each have apertures therein overlying the apertures (405) in the first layer (404). The apertures in the supporting film (403) and adhesive layer (402) are of approximately the same size, shape and location as the apertures (405) in the first layer. A polymeric backing film (401) is adhered to the adhesive layer (402), the backing layer being continuous, in that it extends over and covers each of the apertures in the first layer; the polymeric backing film corresponds to the second layer described herein. In another embodiment, the adhesive comprising an acrylic polymer of FIG. 4 may be replaced with an adhesive comprising a polyurethane or a hydrogel with low water absorption.

Before use on a wound, the composition may have a removable release liner covering the adhesive surface of the first layer and/or on a non-wound facing surface of the second layer. The release liner on the first and/or second layer may be removed before the composition is applied to a wound. The outer surface of the second layer is not typically adhesive, so an adhesive, such as a pressure sensitive adhesive, may be applied to any release liner applied to the second layer, the adhesive on the release liner remaining on the release liner when it is removed from the second layer.

EXAMPLES

The present invention will now be further described with reference to the following non-limiting Examples. The aim of these Examples was to evaluate whether the size and design of apertures in a dressing can have a significant effect on its performance. In particular, an in depth study of the fluid handling properties of dressings according to the disclosure herein compared to products with smaller/no holes that are designed to be in a uniform pattern was performed (please see Examples 1-7 listed below). The dressings' performance will also be studied from a qualitative viewpoint—whether or not the apertures affect the translucency of the dressing is an important factor in a professional wound-monitoring product.

Example 1

Silicone-Containing Dressing—'Square Shape' (013815e)

A central array of 27 apertures was cut into a 75 mm×75 mm sheet of trilaminate silicone adhesive (RAP10449A, Raleigh Coatings) comprising a 30 μm polyurethane film having on one side a 30 g/m$^2$ layer of acrylic pressure sensitive adhesive and on the other side a 145 g/m$^2$ layer of silicone gel. The array of apertures was substantially as shown in FIG. 1A. The mean area occupied by the apertures was approximately 29 mm$^2$. The perimeter of the array was 55 mm long by 55 mm wide. The apertures ranged in size and shape but were no smaller than 5 mm long by 5 mm wide. A 75 mm×75 mm sheet of 30 μm polyurethane film (Inspire 2304, Coveris) was laminated onto the acrylic side of the pre-cut trilaminate silicone adhesive, ensuring all liners were removed.

Example 2

Perforated Silicone with PU Backing, 'Square Shape' (034615a; Comparative Example)

A 75 mm×75 mm sheet was taken of perforated silicone, with perforations 2.8 mm in diameter (Soft Pro 6054, Scapa Healthcare), comprising a 40 μm polyurethane film having on one side a 40 g/m$^2$ layer of acrylic medical grade adhesive and on the other side a layer of transparent medical grade silicone gel. A 75 mm×75 mm sheet of 30 μm polyurethane film (Inspire 2304, Coveris) was laminated onto the acrylic side of the perforated silicone trilaminate, ensuring all liners were removed.

Example 3

Silicone-Containing Dressing—'Oval Shape' (034515a)

A linear array of 9 apertures was cut into a 150 mm×80 mm oval of trilaminate silicone adhesive (RAP10449A, Raleigh Coatings) comprising a 30 μm polyurethane film having on one side a 30 g/m$^2$ layer of acrylic pressure sensitive adhesive and on the other side a 145 g/m$^2$ layer of silicone gel. The perimeter of the array was 115 mm long and 54 mm wide. The apertures ranged in size and shape but were no smaller than 10 mm long and 25 mm wide. The array of apertures was substantially as shown in FIG. 1B. The mean area occupied by the apertures was approximately 306 mm$^2$. A 150 mm×80 mm oval of 30 μm polyurethane film (Inspire 2304, Coveris) was laminated onto the acrylic side of the pre-cut trilaminate silicone adhesive, ensuring all liners were removed.

Example 4

Perforated Silicone with PU Backing, 'Oval Shape' (034515b; Comparative Example)

A 150 mm×80 mm oval was taken of perforated silicone trilaminate, with perforations 2.8 mm in diameter (Soft Pro 6054, Scapa Healthcare), comprising a 40 μm polyurethane film having on one side a 40 g/m$^2$ layer of acrylic medical grade adhesive and on the other side a layer of transparent medical grade silicone gel on the other side. A 150 mm×80 mm sheet of clear 30 μm polyurethane film (Inspire 2304, Coveris) was laminated onto the acrylic side of the perforated silicone trilaminate, ensuring all liners were removed.

Example 5

Sheet Hydrocolloid (034515a; Comparative Example)

A 70 mm×70 mm square was cut from a hydrocolloid roll (143004-67, Europeed), ensuring all liners were removed.

Example 6

Hydrocolloid-Containing Dressing (043515c)

A 70 mm×70 mm square of transfer adhesive (RX1348U, Scapa Healthcare) was laminated onto the polyurethane side of a 70 mm×70 mm square of hydrocolloid (143004-67, Europeed—this being a polyurethane sheet having a continuous layer of hydrocolloid thereon). A central array of 12 ovals was cut into this composition. The perimeter of the array was 34 mm long and 53 mm wide and the apertures were 6 mm long and 8 mm wide. A 70 mm×70 mm sheet of clear 30 μm polyurethane film (Inspire 2304, Coveris) was laminated onto the transfer adhesive, ensuring all liners were removed.

Example 7

It is possible to prepare a dressing similar to that described in Example 1 but replacing the silicone adhesive with a pressure sensitive adhesive comprising an acrylic polymer or a pressure sensitive adhesive comprising a polyurethane.

Example 8

Open WRAP Test Rig

This experiment used samples with lot numbers 013815e (Example 1) and 034615a (Example 2, reference), listed above.

Aim

This experiment set out to determine the time period (in hours) it would take for a dressing according to the present disclosure to fail, when compared to a perforated silicone dressing with non-adhesive PU backing.

Summary of the Method

This was assessed by using the WRAP test rig (Surgical Materials Testing Laboratory), following the instructions listed below. Blue calcium saline solution was pumped into the apparatus at a rate of 0.3 ml/h and this was run until the dressing failed (recorded via computer), up to a maximum time limit of 24 hours. The number of hours it took for each dressing to fail was then recorded and compared. The criterion for failure was when the saline solution could no longer be handled by the dressing. This caused it to drip into the apparatus outlet pipe, therefore falling onto the balance below to alter its weight—which was picked up by the data logger and converted into graphical form (see results in FIG. 5). This was tested at 20° C. and <40% relative humidity.

Apparatus Required

Electronic top-pan balance with integral RS232 serial interface (a calibrated balance is preferable)
WRAP Test Rig
Electronic data logger and appropriate interface to capture data from the balance
Delivery system for test solution (Graseby 3100 Syringe Pump)
Supply of 47 mm diameter cellulosic absorbent pads (Millipore Catalogue Number AP1004700)
Fluid collection vessel with small surface area
Blue calcium saline solution: A stock solution of calcium saline was created by using 0.675-0.725 g $CaCl_2$ (Sigma-Aldrich) added to 20.25-21.25 g $NaCl_2$ (Fisher), made up to 2,500 ml with pure water. 1 litre of blue solution was then made up from 4.37 g dye (Royal Blue Dye, Sugarflair) added to 997 ml of the stock calcium saline solution
Light machine oil or similar lightweight oil
Tweezers
Gloves
Supply of absorbent tissue
Supply of 60 ml syringes for syringe pump
De-ionised water (for cleaning)
Isopropanol (for cleaning)
Small Petri dishes (or similar containers)

Method

1. Place the balance on the bottom tier of the support table and level.
2. Turn the balance on and leave for at least 30 minutes to settle.
3. Zero the balance.
4. Connect the data logger to the balance and set up the data logger to record for the required time period at a rate of a least one reading every five minutes.
5. Place a suitable collecting vessel on the top pan balance; the collecting vessel should have a small amount of test solution covered with a layer of light machine oil on the surface to prevent evaporation loss.
6. Fill the fluid delivery system with blue calcium saline solution, ensuring all air bubbles are removed and there is sufficient fluid in the system to complete the experiment at the required flow rate.
7. Set the fluid delivery system to the required flow rate, connect to the platform and purge until the fluid starts to fill the channel in the centre of the depression in the platform.
8. Stop the fluid delivery system and remove any excess fluid from the channel using absorbent tissue.
9. Place two absorbent pads in the central depression of the testing platform.
10. Using the fluid delivery system, purge with 2 ml of fluid twice, ensuring the pads are fully wetted.
11. Dry the outlet tube to remove any fluid that may not have fully dropped over.
12. Place the dressing to be tested centrally over the pads.
13. Tare the balance and start the data logger/fluid delivery system and run for the required time period, make a note of the start and finish time.
14. Upon experiment completion, stop the data logger and fluid delivery system, read the display on the delivery system (to confirm the amount of fluid delivered) and download the data logger.
15. Remove dressing/absorbent pads from the system and dispose, clean the central depression on the testing platform with purified water and isopropanol before starting another test.

Results

Figure 5:
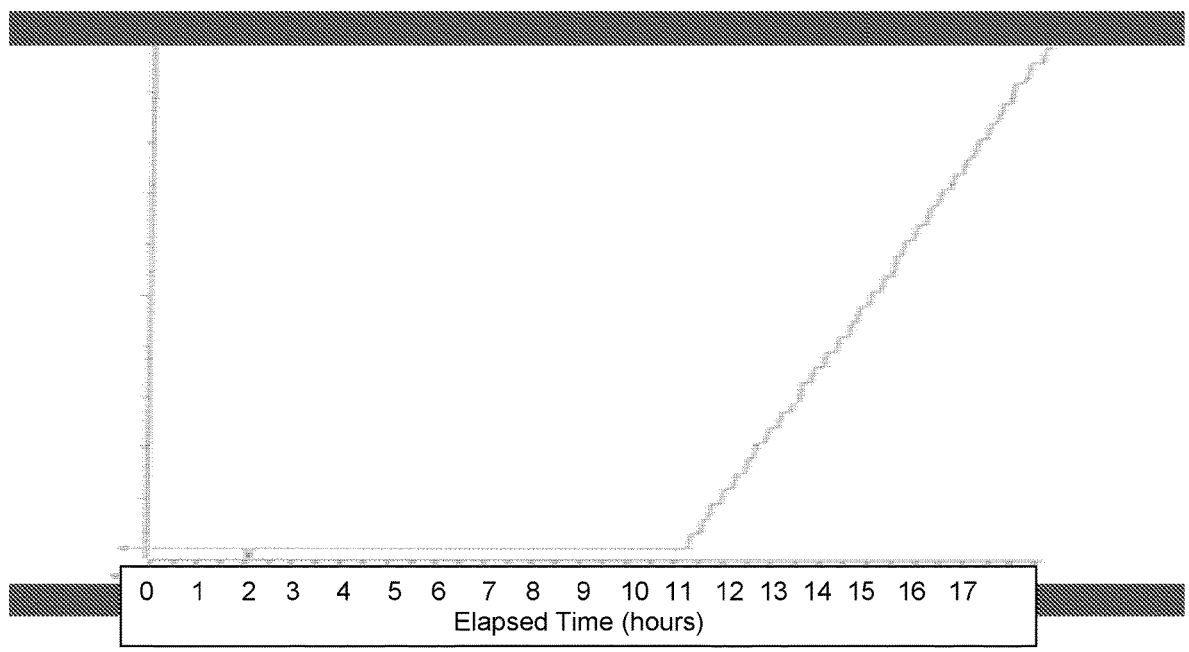
FIG. 5 shows the results of the experiment described in Example 8.
Figure 5:
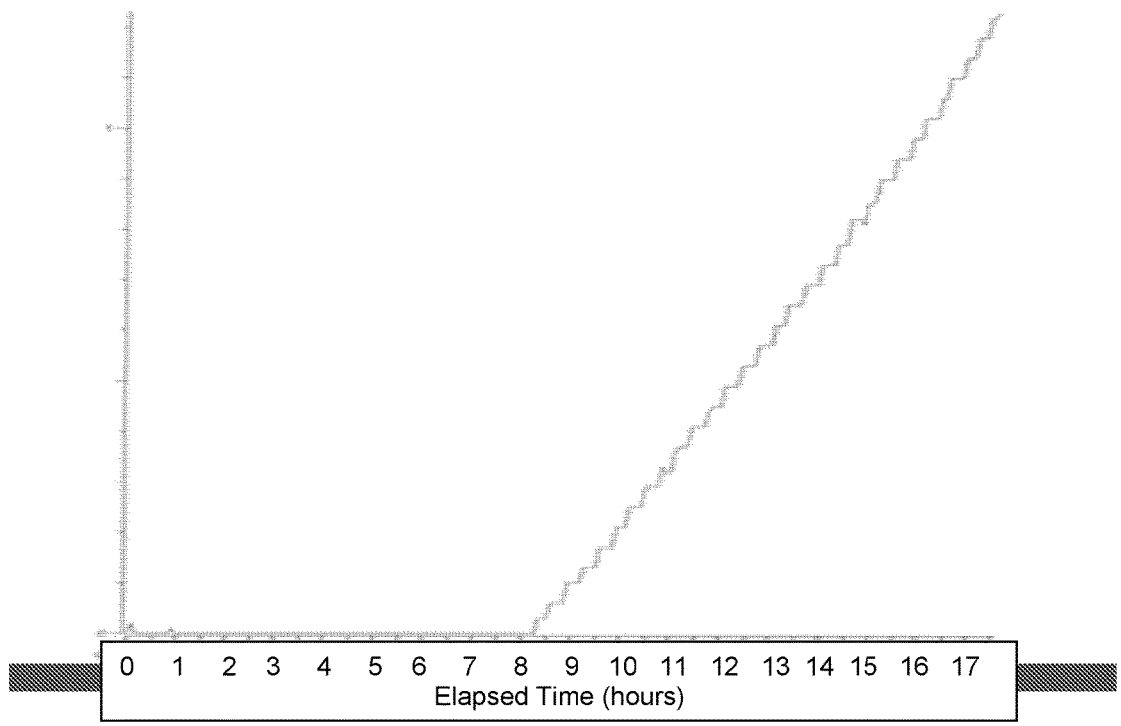

The results are displayed in FIG. 5.

Comments

As can be seen from the graphs shown in FIG. 5, the sample according to the present disclosure (Example 1) took 3 hours longer to reach failure than the perforated silicone sample (Example 2). This result may be considered surprising considering the percentage of open area on the dressing of Example 1 was calculated to be 17%, compared to 37% on the perforated silicone sample (Example 2). Therefore, higher levels of MVTR (and overall fluid handling) were expected on the perforated silicone sample (Example 2). This data shows that the dressing according to the present disclosure provides an unexpected improvement in fluid handling properties.

Example 9

Blocked WRAP Test Rig

This experiment used samples with lot numbers 013815e (Example 1) and 034615a (Example 2), listed above.

Aim

This experiment was a qualitative study into the effects that hole size and design had on the time taken for fluid to 'track' to the edges of a dressing and therefore causing the dressing to lose adhesion, leak, and ultimately fail.

Summary of the Method

This was assessed by using the WRAP test rig (Surgical Materials Testing Laboratory), following the instructions listed below. Blue calcium saline solution was pumped into the apparatus at a rate of 0.5 ml/h and this was continued until the dressing failed, up to a maximum time limit of 24 hours. The number of hours it took for each dressing to fail was then recorded and compared. The criterion for failure was that fluid would track to the edge and leak out the side of the dressing. This was tested at 20° C. and <40% relative humidity.

Apparatus Required

Delivery system for test solution (Greasby 3100 Syringe Pump)
WRAP test rig
Supply of 47 mm diameter cellulosic absorbent pads (Millipore Catalogue Number AP1004700)
Blue calcium saline solution: A stock solution of calcium saline was created by using 0.675-0.725 g $CaCl_2$ (Sigma-Aldrich) added to 20.25-21.25 g $NaCl_2$ (Fisher), made up to 2,500 ml with pure water. 1 litre of blue solution was then made up from 4.37 g dye (Royal Blue Dye, Sugarflair) added to 997 ml calcium saline solution
Artery forceps
Supply of 60 ml syringes for syringe pump
Supply of absorbent tissue
De-ionised water (for cleaning)
Isopropanol (for cleaning)

Small Petri dishes (or similar containers)
Method
1. Apply artery forceps to the outlet pipe.
2. Fill the fluid delivery system with blue calcium saline solution; ensuring all air bubbles are removed and there is sufficient fluid in the system to complete the experiment at the required flow rate.
3. Set the fluid delivery system to the required flow rate, connect to the platform and purge until the system starts to fill the channel in the centre of the depression in the platform.
4. Stop the fluid delivery system and remove any excess fluid from the channel using absorbent tissue.
5. Place two absorbent pads in the central depression of the testing platform.
6. Using the fluid delivery system, purge with 2 ml of fluid twice, ensuring the pads are fully wetted.
7. Place the dressing to be tested centrally over the pads.
8. Start the fluid delivery system and run for the required time period, making a note of the start and finish time.
9. Upon experiment completion, stop the fluid delivery system and read the display (to confirm the amount of fluid delivered).
10. Remove the dressing/absorbent pads from the system and dispose, clean the central depression on the testing platform with purified water and isopropanol before starting another test.

Figure 6:
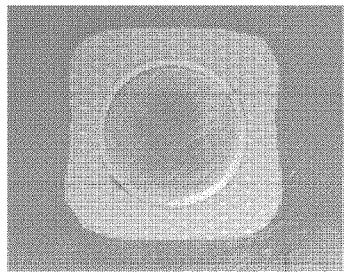
FIG. 6 shows the results of the experiment described in Example 9.
Figure 6:
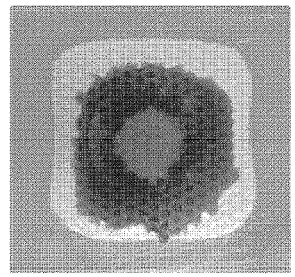
Figure 6:
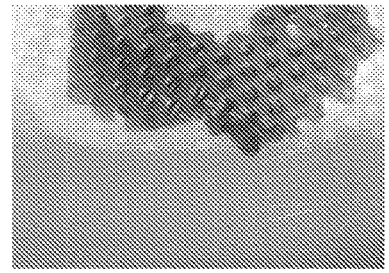
Figure 6:
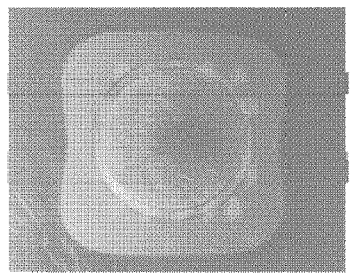
Figure 6:
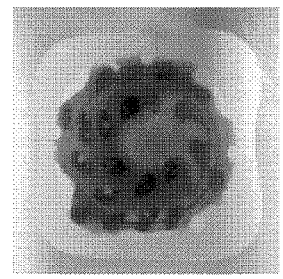
Figure 6:
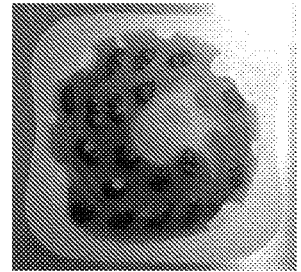

Results
The results are displayed in FIG. 6.

Comments
As the images in FIG. 6 show, the dressing of Example 1 was able to manage significantly higher levels of fluid despite having 20% less open area. This may be due to the design of the apertures holding the fluid centrally within the dressing, leaving less opportunity for it to 'track' to the edges. This factor may enhance the wear time of the product, allowing stronger adhesion around the edges of the dressing.

Example 10

Comparison of Translucency

This experiment used samples with lot numbers 013815e (Example 1) and 034615a (Example 2), listed above.
Aim
This experiment aimed to see whether the apertured design of the silicone product according to the present disclosure makes the wound bed underneath more visible, in comparison to reference dressing.
Summary of the Method
The samples used were dried out and stuck to a page of lined paper (each containing equal amounts of blue calcium saline solution in the same area of the dressing)—see FIG. 7. These dressings were than examined by 12 participants ranging in age and gender, and it was noted which was deemed 'more translucent'.
Apparatus Required
Blue calcium saline solution: A stock solution of calcium saline was created by using 0.675-0.725 g $CaCl_2$ (Sigma-Aldrich) added to 20.25-21.25 g $NaCl_2$ (Fisher), made up to 2,500 ml with pure water. 1 litre of blue solution was then made up from 4.37 g dye (Royal Blue Dye, Sugarflair) added to 997 ml calcium saline solution
Paddington cups
Lined paper Method
1. Add 20 ml of blue calcium saline solution to the Paddington cup.
2. Add sample centrally to cup and replace lid.
3. When all samples have been prepared, place on a tray and invert the cups.
4. Leave samples for 10 minutes at room temperature, then turn the cups upright.
5. Remove samples from cups and leave at room temperature to dry out for one hour.
6. Stick samples to lined paper.
7. Participants should be shown these samples and asked to choose the one deemed more translucent.

Figure 7:
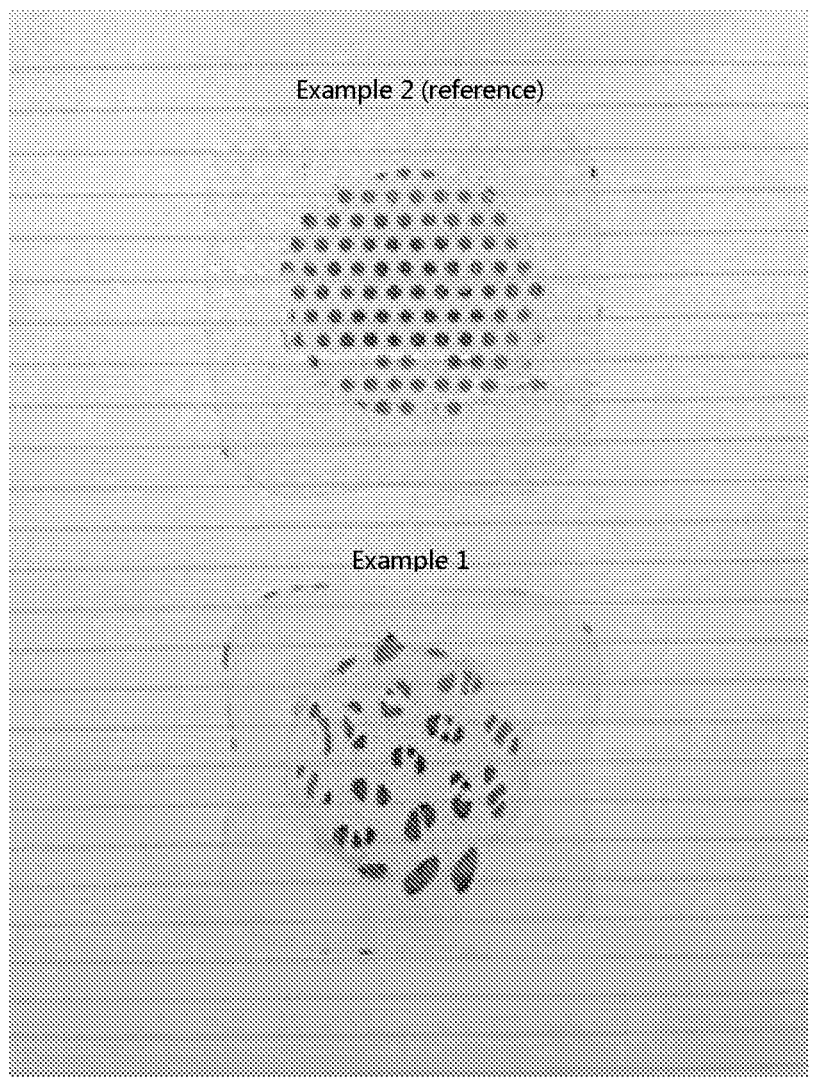
FIG. 7 shows the results of the experiment described in Example 10.

Results
The samples are displayed in FIG. 7.

|  | Example 1 | Example 2 (reference) |
|---|---|---|
| Number of Participants | 10 | 2 |
| Percentage of Participants | 83 | 17 |

Comments
The results above show that over 80% of participants from a sample size of 12 agree that the difference in aperture size and arrangement significantly improves the translucency of the product. This is an important factor of the dressing as it acts primarily as a wound-monitoring device, so signs of infection must be easily spotted.

Example 11

Comparison of Flexibility

Figure 8:
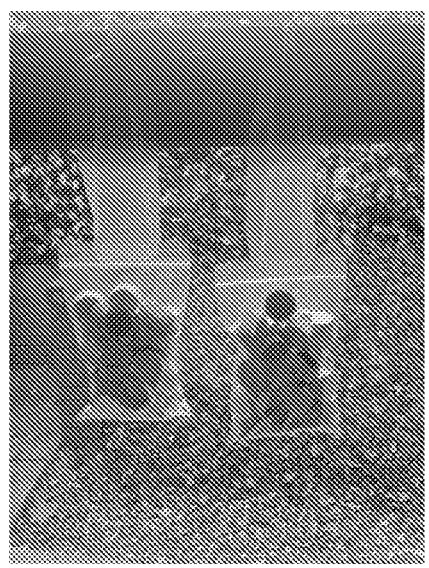
FIG. 8 shows the experimental set-up described in Example 11.

This experiment used samples with lot numbers 034515a (Example 3) and 034515b (Example 4), listed above.
Aim
The aim of this experiment was to look at whether the design and sizing of the apertures has a significant effect on the dressing's flexibility along a particular axis—an important factor for a dressing to be used on the knees/elbows requiring higher longitudinal flexibility.
Summary of the Method
The dressings were both measured before and after being stretched using the methodology below. These measurements were then compared.
Apparatus Required
Binder clips
Polyester zip-lock bags
Objects with a cumulative weight of 175 g
Staples
Method
1. Remove any liners present on the dressing, measure and record its length.
2. Using a binder clip, attach the dressing so that it is hanging vertically from an elevated surface.
3. Place the weights to be used in a polyester bag and use two staples three cm apart to attach the bag to the bottom edge of the dressing (see FIG. 8).
4. Repeat for each dressing and leave to hang for 1 hour.
5. Re-measure the length of the dressings while under the weight to see the total stretch of the dressing.
6. Remove any weight and measure the length of the dressings again, to ensure they have not been permanently deformed.

Results

| Dressing | Original Length (cm) | Length after 1 h with the Weight (cm) | Length after removal of the Weight (cm) |
|---|---|---|---|
| Example 3 | 15 | 15.9 | 15 |
| Example 4 (refernce) | 15 | 15.1 | 15 |

Comments

The difference in the elasticity of the dressings is significant, considering all but the design was kept consistent. Upon removal of the weight, both dressings returned to their original form and did not lose structural integrity. In a direct comparison, there was a difference of 0.8 cm between the two dressing formats. This result could be considered surprising as there is a calculated 4% difference in open area between the two products, with the dressing of Example 3 having a smaller open area of 26% and Example 4 having an open area of 30%. In view of the fact that the polyurethane film is the most flexible material in the dressings, it would be expected that more being exposed should lead to increase in overall elasticity. However, the opposite result was detected.

Example 12

Observation of the Doming Effect

This experiment used samples with lot number 013815e (Example 1) and 034615a (Example 2), listed above.

Aim

The aim of this experiment was to observe the effect that the pressure of fluid had on the stretching of the polyurethane film above the apertures, creating a 'doming' effect in the film. This effect could be helpful to indicate when a dressing change is used for a visually impaired patient.

Summary of the Method

The dressing was applied to the underside of a narrow tube. 15 ml of pure water was added to the tube and the effect the water pressure had on the dressing structure was recorded qualitatively.

Apparatus Required

Supply of pure water

Tube approximately 2.5 cm in diameter

Method
1. Apply the dressing to be tested centrally to the underside of the tube, ensuring the edges of the dressing are pushed to seal against the outer edges of the tube.
2. Add 15 ml of pure water to each tube and hold the tube vertically so that it is elevated.
3. Qualitatively record the effects of the fluid on the structure of the dressing.

Results

Figure 9:
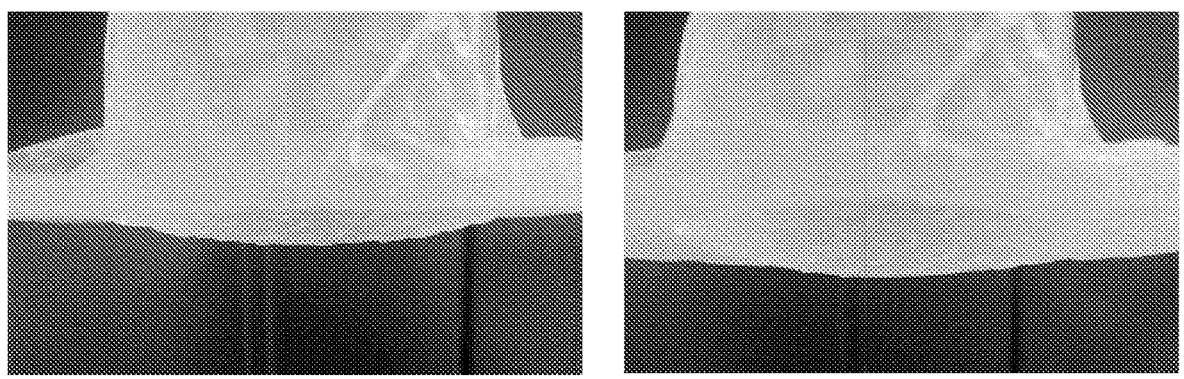
FIG. 9 shows the results of the experiment described in Example 12.
Figure 9:
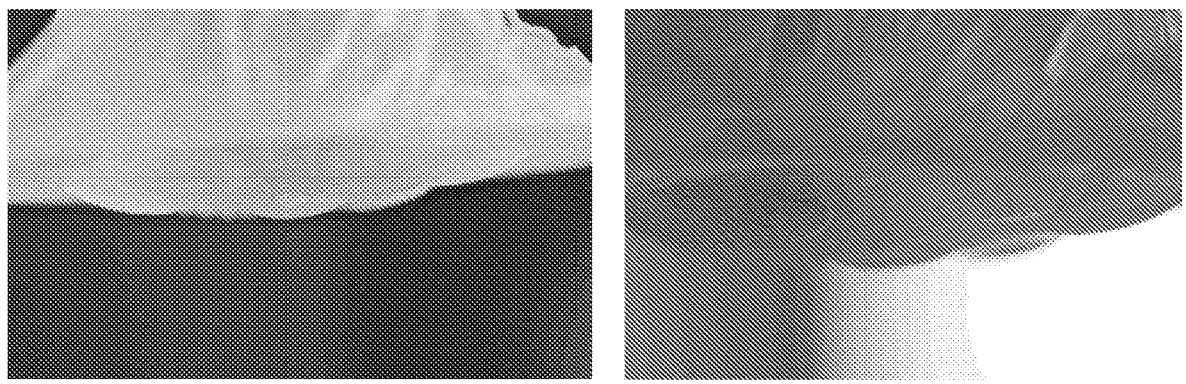
Figure 10:
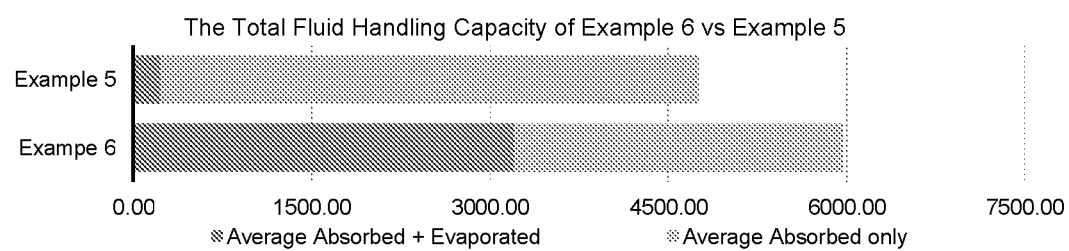
FIG. 10 shows the results of the experiment described in Example 13.

The results are displayed in FIG. 9.

Comments

The images above show that the sizes of the apertures present have a distinct qualitative effect on the levels of 'doming' seen within the product. The samples of Example 2 (reference) showed little-to-no doming, and no tactile difference between the apertures and the rest of the dressing could be distinctly felt. The samples of Example 1, however, showed considerable doming that could be seen visually detected and felt by hand.

Example 13

Comparison of Total Fluid Handling Capacity—Hydrocolloid-Containing Dressings

This experiment used samples with lot numbers 034515a (Example 5) and 043515c (Example 6), listed above.

Aim

To compare the total fluid handling capacity of a hydrocolloid-containing dressing according to the present disclosure against an uncut hydrocolloid sheet, using calcium saline solution.

Summary of the Method

Assessed using 5 inverted Paddington cups for each dressing format, the experiment was carried out at 37° C. and <20% relative humidity.

Apparatus Required

Circle template approximately 5.5 cm in diameter

Scissors

Supply of absorbent tissue

Polyester zip-lock bag

Paddington cups, labeled numerically

Calcium Saline solution: A solution of calcium saline was created by using 0.675-0.725 g $CaCl_2$ (Sigma-Aldrich) added to 20.25-21.25 g $NaCl_2$ (Fisher), made up to 2,500 ml with pure water Tray Humidity cabinet at 37° C., <20% relative humidity Electronic top-pan balance with integral RS232 serial interface (a calibrated balance is preferable)

12.5 cm parafilm strips

Method
1. Lay the sample to be tested down on a flat surface and draw/cut out a circle using the template.
2. Place Paddington cup and all screws required on a balance and record the measurement of the weight.
3. Fill the cup with 20 ml of Calcium Saline solution; record the new measurement of the weight.
4. Add a pre-cut circular sample to the cup and replace the lid, re-record weight.
5. Wrap parafilm around the outer edge of the lid/sample to prevent leaking.
6. Screw the lid of the cup on and record the final weight.
7. When all samples have been prepared, place on a tray and invert the cups.
8. Place the tray into the humidity cabinet and record the start time.
9. After 24 hours, remove the samples and re-record their weight.
10. Open the cup and pour out any excess fluid and using tissue paper carefully dry any remaining fluid within the cup.
11. Re-weigh the Paddington cup.

Results

Average Fluid Handling

| Sample | Average MV Loss | Standard Deviation of MV Loss | Average Absorption | Standard Deviation of Absorption | Average TFHC | Standard Deviation of TFHC |
|---|---|---|---|---|---|---|
| Example 6 (reference) | 222.00 | 13.0 | 4534 | 470.5 | 4756 | 475.8 |
| Example 5 | 3200.00 | 73.1 | 2770 | 159.2 | 5970 | 209.5 |

Comments

The results show that the hydrocolloid-containing samples according to the present disclosure have a significantly higher level of moisture vapour loss, as well as increased total fluid-handling capacity. Both these results have low standard deviations (at <10%), so it can be assumed that they are from separate populations with minimal crossover. Although the absorption levels of the reference Example are higher, this data has a very high standard deviation and so it may not be consistently accurate. These findings can be considered even more significant taking into account that the sample according to the present disclosure has an extra layer of polyurethane film laminated onto it—something that the reference Example did not contain.

Example 14

Testing Water Absorption of Skin Adhesives

In this test, the following samples were used: Raleigh Silicone Adhesive Trilaminate (Examples 1 and 3), Sheet hydrocolloid (Example 5), hydrocolloid+layer of transfer adhesive to make a trilaminate (as described in Example 6) and 40 gsm acrylic PSA coated onto a 40 μm polyurethane film (Inspire 2327), with a layer of transfer adhesive on the opposing side to make a trilaminate. Also tested, as reference examples, were samples of hydrogel (including polymerisation product of the sodium salt of acrylamidomethylpropanesulphonic acid (Na AMPS)—these are denoted 'Rollstock 68 and Rollstock 128 in the table below).

Each adhesive was cut into a 5 cm×5 cm square. This was then weighed (including any liners and associated film layers). After the initial weighing the liners were removed and weighed. The samples were then placed in a beaker containing 200 ml pure water. The samples were left to absorb for a time period of one hour. After which they were re-weighed and the % increase in weight for each sample was calculated. The weight of any film associated with the adhesive was also determined (e.g. from a sample of the film without the adhesive on it), so the weight of the sample (i.e. just the adhesive) without the film and without the liner could be calculated.

| Sample | Weight (+Liners) | Liner Weight | Sample Weight (−Liners and −film) | Sample Weight After Fluid | Percentage Increase |
|---|---|---|---|---|---|
| Silicone | 0.785 | 0.36 | 0.425 | 0.595 | 40% |
| Hydrocolloid | 1.64 | 0.44 | 1.13 | 2.21 | 95% |
| Hydrocolloid + Transfer Adhesive | 2.07 | 0.68 | 1.39 | 2.7 | 94% |
| Acrylic PU Film + Transfer Adhesive | 0.82 | 0.45 | 0.37 | 0.42 | 13% |
| Rollstock 68 | 3.56 | 0 | 3.56 | 32.03 | 799% |
| Rollstock 128 | 2.31 | 0 | 2.31 | 34.53 | 1394% |

This illustrates the low water absorption of pressure sensitive adhesives based on silicone and hydrocolloid, as compared to some hydrogels.

The invention claimed is:

1. A composition for application to a wound, the composition comprising:
    a first layer comprising a skin adhesive with a low water absorption, such that, when immersed in water at 20° C. for a period of 1 hour, the skin adhesive absorbs an amount of water equal to 40% or less of a weight of the skin adhesive,
    wherein the first layer has a wound-facing side and a non-wound-facing side and, in a first area, apertures extend through the first layer from the wound-facing side to the non-wound-facing side, the first layer having a second area that extends to an edge of the composition and forms a perimeter around the first area, the perimeter lacking apertures therethrough, and, in-use, the wound-facing side of the first layer is configured to contact the wound,
    wherein a mean area of the apertures on at least one of the wound-facing side and non-wound-facing side of the first layer is at least 20 mm$^2$; and
    a second layer disposed adjacent to the non-wound-facing side of the first layer, the second layer being an outermost layer of the composition, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2: 2002,
    wherein the composition further comprises a third layer disposed between the first layer and second layer, the third layer comprising a polymeric film and being a supporting layer for the first layer, the third layer having apertures therethrough, substantially corresponding to the apertures in the first layer;
    wherein a fourth layer is disposed between the second layer and the third layer, the fourth layer comprising an adhesive that contacts the second layer and the third layer, the fourth layer also having apertures therethrough substantially corresponding to the apertures in the first and third layer;

and wherein each of the first, second, and third layers extends to the edge of the composition, the third layer being between the first and second layers at the edge.

2. The composition according to claim 1, wherein, for each aperture of the first layer, a shortest distance (X1) from a given aperture in the first layer to an edge of the first layer is more than a shortest distance ($X_2$) between the given aperture and a nearest adjacent aperture.

3. The composition according to claim 2, wherein, for each aperture of the first layer, the ratio X1/X2 is at least 1.5.

4. The composition according to claim 1, wherein the skin adhesive comprises a substance selected from a silicone, a hydrocolloid, a polyurethane, an acrylic polymer, a rubber adhesive, or a hydrogel.

5. The composition according to claim 1, wherein the mean area of the apertures on the at least one of the wound-facing side or the non-wound-facing side of the first layer is from 30 mm² to 50 mm².

6. The composition according to claim 1, wherein a total area occupied by the apertures on the wound-facing side and/or non-wound-facing side of the first layer is 70% or less of a total area of the first layer, and wherein the first layer has from 1 to 5 apertures per square 10 cm of the wound-facing side and/or non-wound-facing side.

7. The composition according to claim 1, wherein the apertures of the first layer are arranged in an array such that there are a plurality of apertures along a direction x across the wound-facing surface of the first layer and a plurality of apertures along a direction y, perpendicular to x, across the wound facing surface of the first layer.

8. The composition according to claim 1, wherein the apertures in the first layer are provided in a single line.

9. The composition according to claim 1, wherein for at least one of the apertures in the first layer, a shortest distance from the at least one aperture in the first layer to an edge of the first layer is 5 mm.

10. The composition according to claim 1, wherein the second layer is transparent and, optionally, the first layer is transparent.

11. The composition according to claim 1, wherein the whole composition is transparent.

12. The composition according to claim 1, wherein the third and fourth layers are both transparent; and wherein the skin adhesive of the first layer comprises a material selected from a silicone, an acrylic, a hydrocolloid, or a polyurethane, and the adhesive of the fourth layer comprises an acrylic polymer.

13. The composition according to claim 1, wherein each of the second layer and third layer comprises a polyurethane film.

14. The composition according to claim 1, wherein for each of the apertures in the first layer, a shortest distance from the aperture in the first layer to an edge of the first layer is at least 3 mm.

15. A method of forming a composition for application to a wound, the method comprising:
providing a first layer comprising a skin adhesive with a low water absorption, such that, when immersed in water at 20° C. for a period of 1 hour, the skin adhesive absorbs an amount of water equal to 40% or less of a weight of the skin adhesive,
wherein the first layer has a wound-facing side and a non-wound-facing side and, in a first area, apertures extend through the first layer from the wound-facing side to the non-wound-facing side, the first layer having a second area that extends to an edge of the composition and forms a perimeter around the first area, the perimeter lacking apertures therethrough, wherein a mean area of the apertures on at least one of the wound-facing side and non-wound-facing side of the first layer is at least 20 mm², the first layer being disposed on a third layer that comprises a polymeric film, the third layer being a supporting layer for the first layer and having apertures therethrough substantially corresponding to the apertures of the first layer, associating a second layer and a fourth layer with the first and third layers, such that the third layer is disposed between the first and second layers and the fourth layer is disposed between the second and third layers, the second layer being an outermost layer of the composition, and, in-use, the wound facing side of the first layer is configured to contact the wound, the second layer comprising a polymeric film that is continuous in that it extends over and covers each of the apertures of the first layer, the second layer having a moisture vapour transmission rate (MVTR) of at least 500 g/m²/24 hours, measured in accordance with BS EN 13726-2:2002;

wherein the fourth layer comprises an adhesive that contacts the second layer and the third layer, the fourth layer also having apertures therethrough substantially corresponding to the apertures in the first and third layers, and wherein each of the first, second, third, and fourth layers extends to the edge of the composition, the third layer being between the first and second layers at the edge and the fourth layer being between the second and third layers at the edge.

16. The method according to claim 15, wherein the method further comprises a step of forming the apertures in the first, third, and fourth layers.

17. The method according to claim 16, wherein, before the formation of each aperture in the first, third, and fourth layers, the first layer is disposed on aside of the third layer and the fourth layer is disposed on another, opposing side of the third layer, and each aperture is formed by cutting through the first, third, and fourth layers, and, after each aperture is formed, the fourth layer is adhered to the second layer.

18. The method according to claim 15, wherein the skin adhesive comprises a substance selected from a silicone, a hydrocolloid, a polyurethane, an acrylic polymer, a rubber adhesive, or a hydrogel.

19. A composition for application to a wound, the composition comprising:
a first layer comprising a skin adhesive comprising a substance selected from a silicone, a hydrocolloid, a polyurethane, an acrylic polymer, a rubber adhesive, or a hydrogel, the substance having a low water absorption such that, when immersed in water at 20° C. for a period of 1 hour, the substance absorbs an amount of water equal to 40% or less of a weight of the substance,
wherein the first layer has a wound-facing side and a non-wound-facing side and, in a first area, apertures extend through the first layer from the wound-facing side to the non-wound-facing side, the first layer having a second area that extends to an edge of the composition and forms a perimeter around the first area, the perimeter lacking apertures therethrough, and, in-use, the wound-facing side of the first layer is configured to contact the wound, wherein a mean area of the apertures on at least one of the wound-facing side and non-wound-facing side of the first layer is at least 20 mm$^2$; and a second layer disposed adjacent to the non-wound-facing side of the first layer, the second layer being an outermost layer of the composition, the second layer comprising a polymeric film that is continuous in that it extends over and covers each of the apertures of the first layer, the second layer having a moisture vapour transmission rate (MVTR) of at least 500 g/m$^2$/24 hours, measured in accordance with BS EN 13726-2: 2002, wherein the composition further comprises a third layer disposed between the first layer and second layer, the third layer comprising a polymeric film and being a supporting layer for the first layer, the third layer having apertures therethrough, substantially corresponding to the apertures in the first layer;

wherein a fourth layer is disposed between the second layer and the third layer, the fourth layer comprising an adhesive that contacts the second layer and the third layer, the fourth layer also having apertures therethrough substantially corresponding to the apertures in the first and third layers; and wherein the third layer abuts the first layer and the second layer at the edge of the composition.

* * * * *

UNITED STATES PATENT AND TRADEMARK OFFICE
CERTIFICATE OF CORRECTION

PATENT NO. : 11,944,521 B2  
APPLICATION NO. : 15/775482  
DATED : April 2, 2024  
INVENTOR(S) : Hugh Semple Munro Page 1 of 1

It is certified that error appears in the above-identified patent and that said Letters Patent is hereby corrected as shown below:

In the Claims

In Claim 17, Column 30, Line 43, delete "aside" and insert -- a side --.

Signed and Sealed this
Twenty-third Day of July, 2024

Katherine Kelly Vidal
*Director of the United States Patent and Trademark Office*